(12) United States Patent
Yin et al.

(10) Patent No.: US 11,925,693 B2
(45) Date of Patent: Mar. 12, 2024

(54) POLYMERIC NANOPARTICLES FOR ENHANCED CANCER IMMUNOTHERAPY

(71) Applicant: The Board of Trustees of the Leland Stanford Junior University, Stanford, CA (US)

(72) Inventors: Qian Yin, Los Altos, CA (US); Yu Wong, Stanford, CA (US); Mark M. Davis, Atherton, CA (US)

( * ) Notice: Subject to any disclaimer, the term of this patent is extended or adjusted under 35 U.S.C. 154(b) by 0 days.

(21) Appl. No.: 16/632,851

(22) PCT Filed: Jul. 27, 2018

(86) PCT No.: PCT/US2018/044165
§ 371 (c)(1),
(2) Date: Jan. 21, 2020

(87) PCT Pub. No.: WO2019/023622
PCT Pub. Date: Jan. 31, 2019

(65) Prior Publication Data
US 2020/0164090 A1    May 28, 2020

Related U.S. Application Data

(60) Provisional application No. 62/537,780, filed on Jul. 27, 2017.

(51) Int. Cl.
| | | |
|---|---|---|
| *A61K 39/395* | (2006.01) | |
| *A61K 9/51* | (2006.01) | |
| *A61K 38/05* | (2006.01) | |
| *A61K 38/16* | (2006.01) | |
| *A61K 38/20* | (2006.01) | |
| *A61K 47/68* | (2017.01) | |
| *A61K 47/69* | (2017.01) | |
| *C07K 16/28* | (2006.01) | |
| *C07K 16/30* | (2006.01) | |
| *A61K 39/00* | (2006.01) | |
| *A61K 45/06* | (2006.01) | |
| *B82Y 5/00* | (2011.01) | |

(52) U.S. Cl.
CPC ........ *A61K 47/6937* (2017.08); *A61K 9/5123* (2013.01); *A61K 9/5153* (2013.01); *A61K 38/05* (2013.01); *A61K 38/164* (2013.01); *A61K 38/2013* (2013.01); *A61K 47/68* (2017.08); *A61K 47/6851* (2017.08); *C07K 16/2818* (2013.01); *C07K 16/30* (2013.01); *A61K 2039/505* (2013.01); *A61K 2039/55533* (2013.01); *A61K 45/06* (2013.01); *B82Y 5/00* (2013.01)

(58) Field of Classification Search
None
See application file for complete search history.

(56) References Cited

U.S. PATENT DOCUMENTS

| | | |
|---|---|---|
| 2010/0055189 A1 | 3/2010 | Hubbell et al. |
| 2011/0104293 A1* | 5/2011 | Pulendran .............. A61K 39/12 424/490 |
| 2011/0293705 A1 | 12/2011 | Irvine et al. |
| 2013/0315831 A1 | 11/2013 | Shi et al. |
| 2015/0174268 A1* | 6/2015 | Li .......................... A61P 35/00 424/178.1 |

FOREIGN PATENT DOCUMENTS

| | | |
|---|---|---|
| CA | 2971419 A1 | 6/2016 |

OTHER PUBLICATIONS

Wang et al., J. of Pharmaceutical Sciences, vol. 9, No. 1, 2007, p. 1-26.*

* cited by examiner

*Primary Examiner* — Yunsoo Kim
(74) *Attorney, Agent, or Firm* — Pamela J. Sherwood; Andrew R. Guzman; Bozicevic, Field & Francis LLP

(57) ABSTRACT

Polymeric nanoparticles comprising a defined set of biologically active agents that provide for targeted stimulation of non-responsive T cells, e.g. T cells involved in cancer, are provided.

5 Claims, 28 Drawing Sheets

Main pro-inflammatory cytokines (IL-6, macrophage inflammatory protein-1a (MIP-1) have consistently been shown to correlate with the systemic inflammatory response syndrome)

POLYMERIC NANOPARTICLES FOR ENHANCED CANCER IMMUNOTHERAPY

CROSS-REFERENCE

This application claims the benefit of U.S. Provisional Patent Application No. 62/537,780 filed Jul. 27, 2017, which application is incorporated herein by reference in its entirety.

BACKGROUND

Recent advances in nanotechnology and biology include the development and application of functional nanoparticles that are physically absorbed or covalently linked to biological molecules such as peptides, proteins, and nucleic acids.

SUMMARY

Method and compositions are provided that relate to polymeric nanoparticles comprising a defined set of biologically active agents that provide for targeted stimulation of non-functional T cells, e.g. anergic or exhausted T cells involved in cancer. The polymeric nanoparticles comprise an encapsulated payload of biologically active agents; and a surface conjugated therapeutic antibody. It is found that a dose of the encapsulated biologically active agents provides for improved efficacy in treating cancer compared to administration of the same biologically active agents as free agents.

The polymeric nanoparticle may be comprised of a biodegradable polymer. In some embodiments the biodegradable polymer is one or more of lactic acid polymers (PLA), glycolic acid polymers (PLG), and poly(lactic-co-glycolic) acid (PLGA).

In some embodiments the encapsulated payload comprises at least one immunostimulatory compound. In some embodiments the encapsulated payload comprises two immunostimulatory compounds. In some embodiments the encapsulated payload comprises three immunostimulatory compounds. The immunostimulatory compound(s) may be selected from toll-like receptor (TLR) agonists, nucleotide-binding oligomerization domain 2 (NOD2) agonists, and cytokines. In some embodiments the at least one immunostimulatory compound is a TLR agonist. In some embodiments the TLR agonist is a TLR2 agonist.

In some embodiments a cytokine is a pro-inflammatory cytokine, e.g. a cytokine that stimulates T cell activity. The pro-inflammatory cytokine may include, without limitation, one or a combination of interleukin 2 (IL-2), interferon gamma (IFNγ), tumor necrosis factor alpha (TNFα), interleukin 6 (IL-6), interleukin 12 (IL-12), interleukin 7 (IL-7), and interleukin 15 (IL-15), or analogs, derivatives and mimetics thereof. In some embodiments a pro-inflammatory cytokine is IL-2.

In some embodiments the surface conjugated therapeutic antibody specifically binds to a molecule present on the surface of T cells. In some embodiments the therapeutic antibody activates T cells by binding to a component of the TCR or a co-stimulatory protein. In some embodiments, the therapeutic antibody is an agonist antibody that binds to and activates a co-stimulatory protein, which co-stimulatory proteins include, without limitation, CD28, CD27, inducible co-stimulator (ICOS), OX40, glucocorticoid-induced TNFR family related gene (GITR), CD137 (4-1BB), and T-cell immunoglobulin and mucin domain 1 (TIM-1). In some embodiments the therapeutic antibody is an anti-CD28 agonist antibody.

In some embodiments, the polymeric nanoparticle that comprise an encapsulated payload of biologically active agents and a surface conjugated therapeutic cause an increase in expression of MHC class II in tumor dendritic cells. In some embodiments, such polymeric nanoparticles increase the uptake efficiency of TLR2 or NOD2 agonists by dendritic cells. In some embodiments, such polymeric nanoparticles increase NF-κB activity in macrophages. The activation and maturation of tumor dendritic cells and macrophages caused by such polymeric nanoparticles leads them to efficiently present antigen to T lymphocytes, thus initiating an adaptive immune response.

The methods of treatment may comprise administration of additional immunotherapeutic agents, e.g. a second antibody that binds to a tumor antigen, e.g., a cancer cell marker; an immune checkpoint inhibitor an immune costimulatory agonist; a marker of chronic infection; and the like. In some embodiments polymeric nanoparticles are administered in a combination therapy with an effective dose of an immunoregulatory agent, e.g. an antibody binds to and inhibits activity of an immune checkpoint protein. In some embodiments polymeric nanoparticles are administered in a combination therapy with an effective dose of a purified tumor antigen, e.g. a soluble tumor associated protein or fragment thereof.

In some embodiments an effective dose of an immunoregulatory modulating agent is administered in combination with an effective dose of the polymeric nanoparticle. The immunoregulatory modulating agent may be conjugated to the nanoparticle or may not be conjugated to the nanoparticle. In some embodiments the immunoregulatory agent is an agent that inhibits an immune, e.g. T cell, checkpoint protein. In some embodiments the agent is an antibody. In some embodiments the antibody binds to and inhibits activity of a T cell checkpoint protein, which proteins include without limitation PD1; PD-L1; cytotoxic T-lymphocyte-associated protein 4 (CTLA-4); B- and T-lymphocyte attenuator (BTLA); lymphocyte activation gene 3 (LAG3); T-cell immunoglobulin and mucin domain 3 (TIM-3); and V-domain Immunoglobulin Suppressor of T cell Activation (VISTA). In some embodiments an antibody that binds to and inhibits PD-1 or PD-L1 is administered in combination with the polymeric nanoparticle.

The subject nanoparticles find use in various therapeutic methods, e.g. for the treatment of diseases associated with T cell non-responsiveness, including without limitation the treatment of cancer. In some embodiments methods are provided for treatment of a cancer, which cancer is a solid tumor. In some embodiments a solid tumor is one of a carcinoma, sarcoma, lymphoma, myeloma, cancers of the central nervous system, e.g. glioma, medulloblastoma, astrocytoma, etc.

In some embodiments of method of treatment is provided, comprising contacting an individual with an effective dose of polymeric nanoparticles described herein, wherein the effective dose provides for activation of tumor-specific CD8$^+$ T cells, and reduces the growth of tumor cells by increased targeted killing of tumor cells. Treatment may be systemic or localized, e.g. delivery by intratumoral injection, etc.

In some embodiments a pharmaceutical formulation is provided, e.g. for use in the treatment of a human subject, where the formulation comprises a polymeric nanoparticle as described herein, with pharmaceutically acceptable excipient. The pharmaceutical formulation may be provided as a unit dose, e.g. as a sterile pre-pack in a unit dose with diluent and delivery device, e.g. inhaler, syringe, etc. Pharmaceutical compositions or kits may further comprise a second agent, e.g. an antibody, that binds to a second antigen, e.g., a cancer cell marker, an immune checkpoint inhibitor, an immune costimulatory agonist, a marker of chronic infection, and the like. Pharmaceutical compositions or kits may further comprise a tumor antigen, e.g. a soluble tumor associated protein or fragment thereof.

The result provided herein demonstrate in a cancer model that treatment with the polymeric nanoparticles described herein elicited a potent anti-tumor immune response with markedly increased cancer-specific effector $CD8^+$ T cells in the tumor tissue, resulting in significantly delayed tumor growth. In addition, the polymeric nanoparticles can be combined with the immunoregulatory modulating strategies such as checkpoint blocking antibodies to achieve a more potent anti-tumor immune response than either the polymeric nanoparticles or the immunoregulatory modulating strategies alone provide. The combination may also achieve an additive effect or a synergistic effect, and may significantly prolong overall survival.

In certain embodiments, the polymeric nanoparticle comprises an encapsulated payload of IL-2, a TLR2 agonist, a NOD2 agonist and a surface conjugated antibody that specifically binds to and activates CD28. In some embodiments the nanoparticles lack additional active agents.

μg of anti-CD28 Ab and 20 μg of TRP2 peptide for boosting). Tumor infiltrating T cells were isolated for analysis on Day 17.

Figure 10:
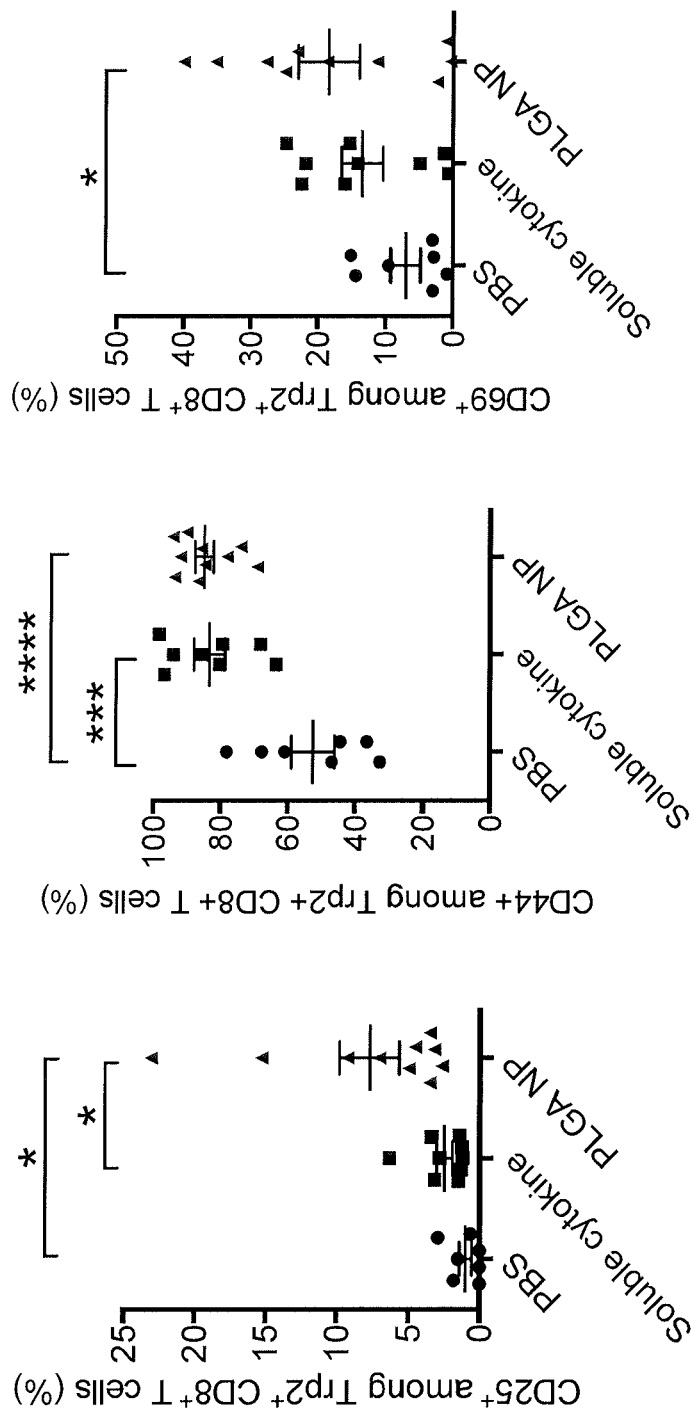

FIG. 10. stimulatory PLGA NPs elicit potent T cell response in tumor by activating the self-specific (TRP2$^+$) CD8$^+$ T cells in tumor. The activation marker (CD25, CD44 and CD69) were significantly unregulated after treatment with stimulatory PLGA NPs. Tumor inoculation was at Day 0, and two treatments were performed at Day 5 (Equivalent dose: 40 ng of IL-2, 2.5 μg of TLR2 agonist, 2.5 μg of NOD2 agonist, 10 μg of anti-CD28 Ab and 10 μg of TRP2 peptide for priming) and Day 11 (Equivalent dose: 80 ng of IL-2, 5 μg of TLR2 agonist, 5 μg of NOD2 agonist, 20 μg of anti-CD28 Ab and 20 μg of TRP2 peptide for boosting). Tumor infiltrating T cells were isolated for analysis on Day 17.

Figure 11:
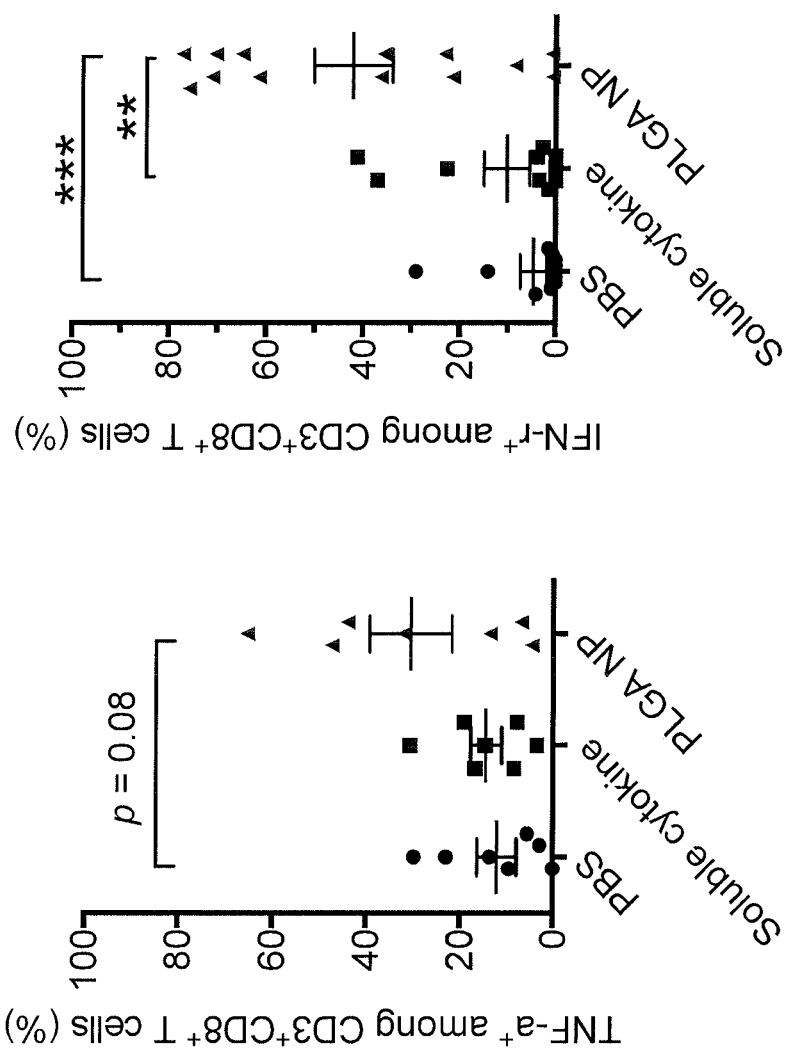

FIG. 11. stimulatory PLGA NPs induce expansion of TNF-α and IFN-γ producing CD8$^+$ population in tumor after treatment with stimulatory PLGA NPs. Tumor inoculation was at Day 0, and two treatments were performed at Day 5 (Equivalent dose: 40 ng of IL-2, 2.5 μg of TLR2 agonist, 2.5 μg of NOD2 agonist, 10 μg of anti-CD28 Ab and 10 μg of TRP2 peptide for priming) and Day 11 (Equivalent dose: 80 ng of IL-2, 5 μg of TLR2 agonist, 5 μg of NOD2 agonist, 20 μg of anti-CD28 Ab and 20 μg of TRP2 peptide for boosting). Tumor infiltrating T cells were isolated for analysis on Day 17.

Figure 12:
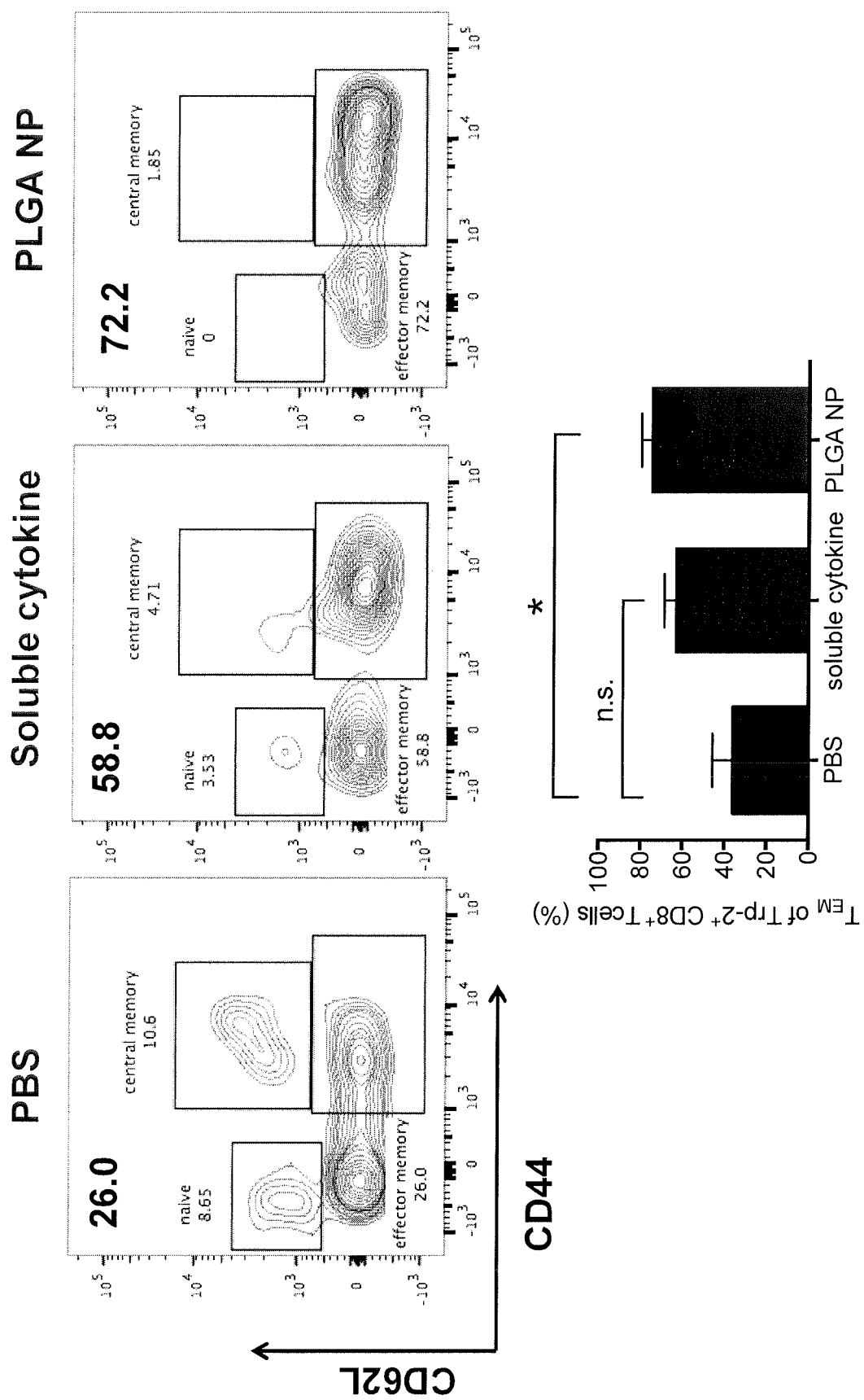

FIG. 12. stimulatory PLGA NP drives T cell response strongly biased toward effector memory (CD44hiCD62Llo) populations in tumor. Tumor inoculation was at Day 0, and two treatments were performed at Day 5 (Equivalent dose: 40 ng of IL-2, 2.5 μg of TLR2 agonist, 2.5 μg of NOD2 agonist, 10 μg of anti-CD28 Ab and 10 μg of TRP2 peptide for priming) and Day 11 (Equivalent dose: 80 ng of IL-2, 5 μg of TLR2 agonist, 5 μg of NOD2 agonist, 20 μg of anti-CD28 Ab and 20 μg of TRP2 peptide for boosting). Tumor infiltrating T cells were isolated for analysis on Day 17 (n=3).

Figure 13:
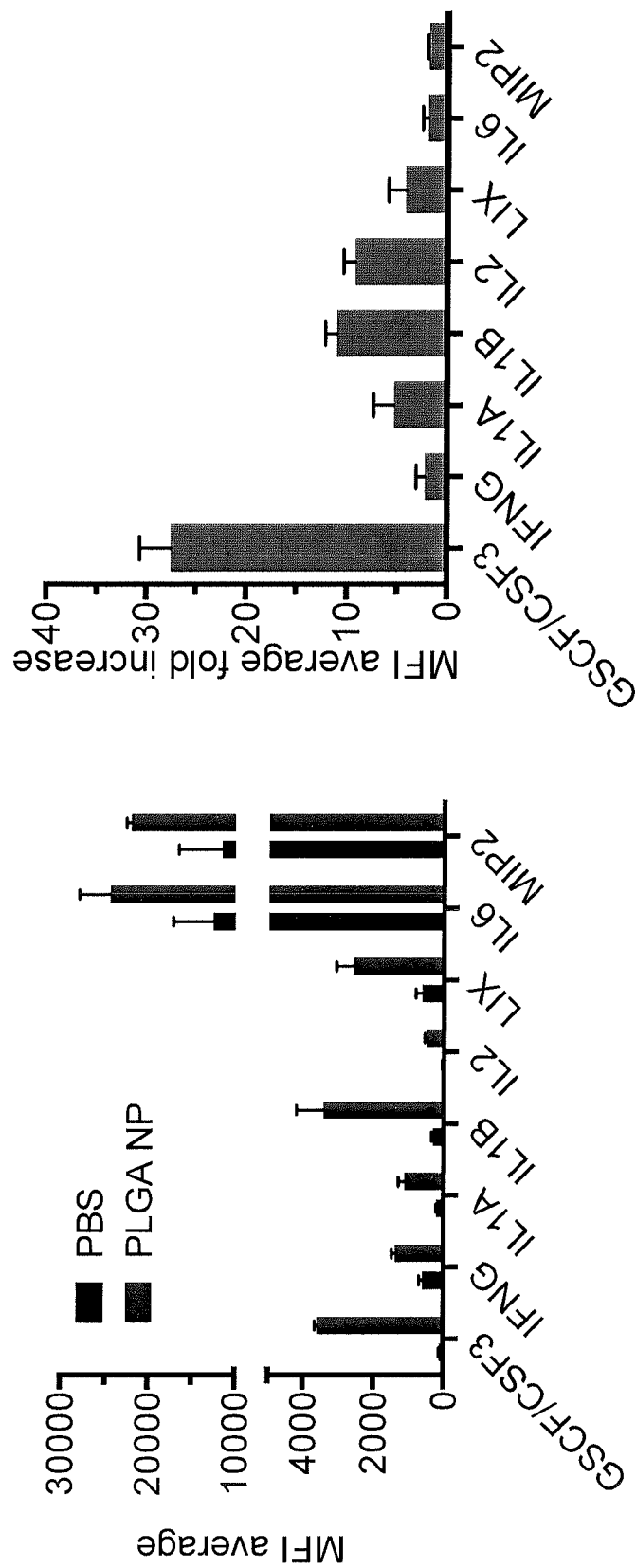

FIG. 13. stimulatory PLGA NP remodels the microenvironment of established tumor by increasing a vast majority of pro-inflammatory cytokines. Tumor inoculation was at Day 0, and two treatments were performed at Day 5 (Equivalent dose: 40 ng of IL-2, 2.5 μg of TLR2 agonist, 2.5 μg of NOD2 agonist, 10 μg of anti-CD28 Ab and 10 μg of TRP2 peptide for priming) and Day 11 (Equivalent dose: 80 ng of IL-2, 5 μg of TLR2 agonist, 5 μg of NOD2 agonist, 20 μg of anti-CD28 Ab and 20 μg of TRP2 peptide for boosting). Tumor infiltrating T cells were isolated for analysis on Day 17 (n=3). GCSF: Granulocyte colony-stimulating factor, stimulate the survival, proliferation, differentiation and function of neutrophil precursors and neutrophils. LIX: LPS-induced CXC chemokine (closely related to human CXCL5, is pro-inflammatory chemokine and is chemotactic for neutrophils). IL-1beta is produced by activated macrophage and dendritic cells, which is presumably in response to TLR and NOD signaling as result of activation of NF-KB pathway and those produced cytokines in turn will influence the subsequent adaptive immune response.

Figure 14:
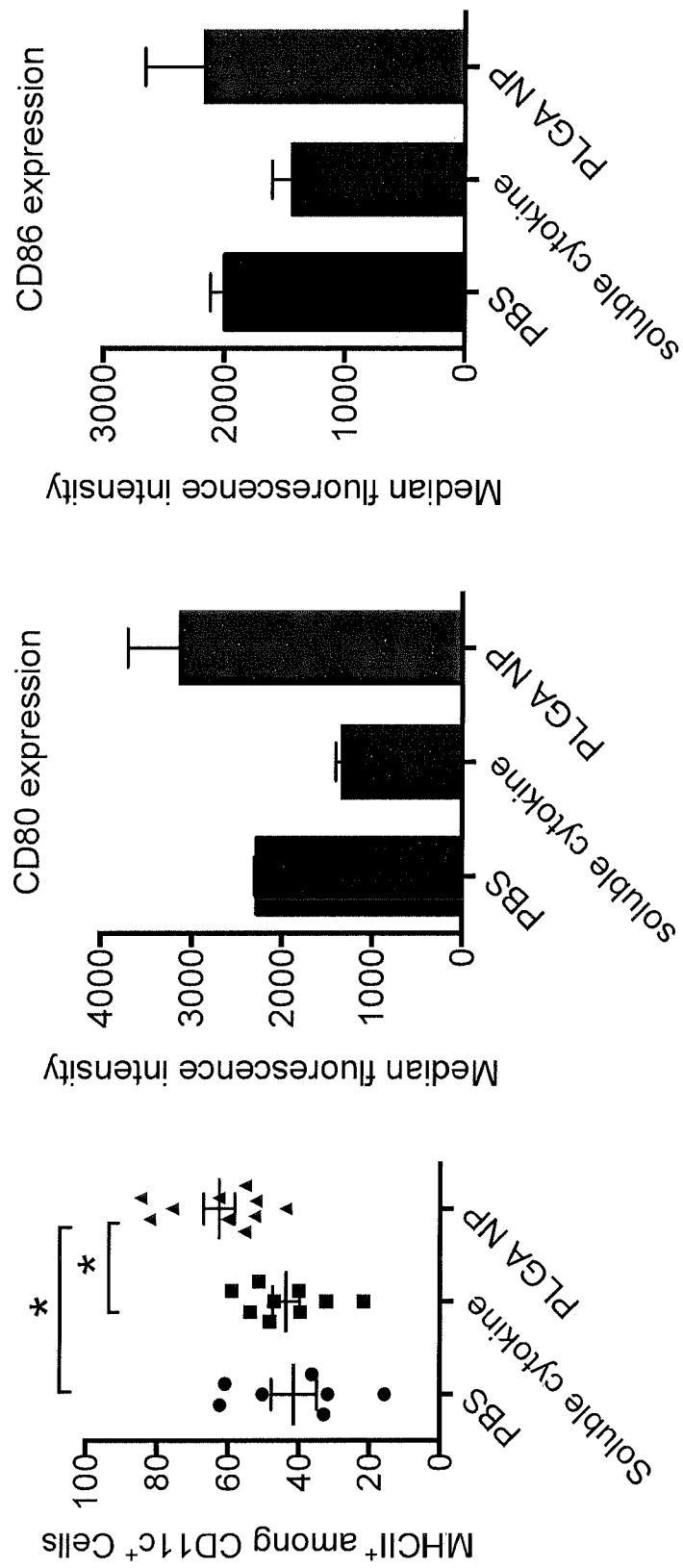

FIG. 14. stimulatory PLGA NPs enhance antigen presentation and activation of DC (CD80, CD86) in tumor. Tumor inoculation was at Day 0, and two treatments were performed at Day 5 (Equivalent dose: 40 ng of IL-2, 2.5 μg of TLR2 agonist, 2.5 μg of NOD2 agonist, 10 μg of anti-CD28 Ab and 10 μg of TRP2 peptide for priming) and Day 11 (Equivalent dose: 80 ng of IL-2, 5 μg of TLR2 agonist, 5 μg of NOD2 agonist, 20 μg of anti-CD28 Ab and 20 μg of TRP2 peptide for boosting). Tumor infiltrating T cells were isolated for analysis on Day 17 (n=3).

Figure 15:
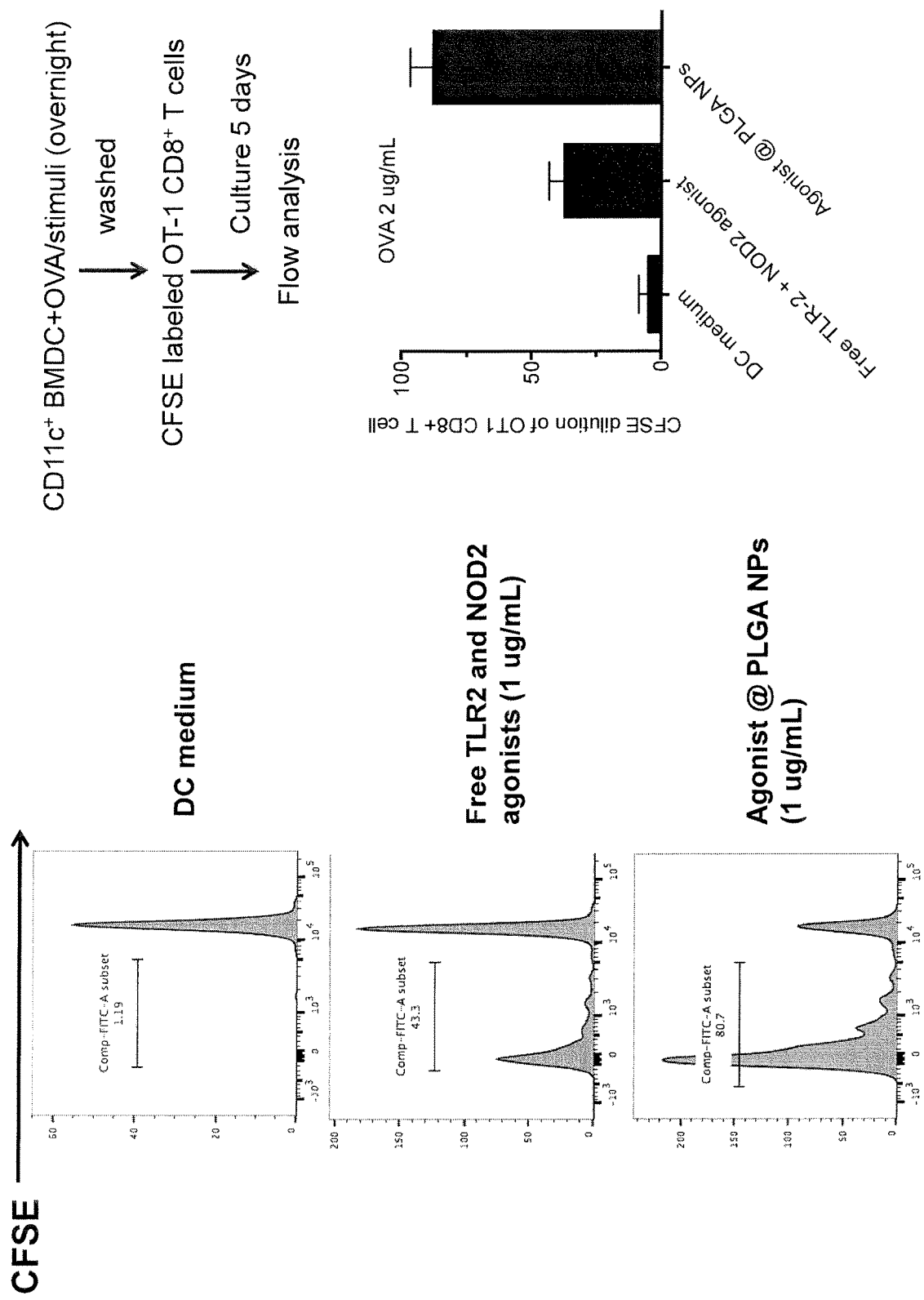

FIG. 15. Bone marrow derived immature dendritic cells (BMDC) were incubated overnight with 2 μg/mL of OVA and maturation stimuli (agonist at 1 μg/mL)(or DC medium alone). DCs were washed 3 times and co-cultured with 30,000 CFSE-labeled OT-I CD8$^+$ T cells. Cells were collected after 5 days of co-culture. Extent of proliferation was quantified by determining the % of cells that had undergone division by determining % of viable CD8$^+$ T cells that had diluted CFSE.

Figure 16:
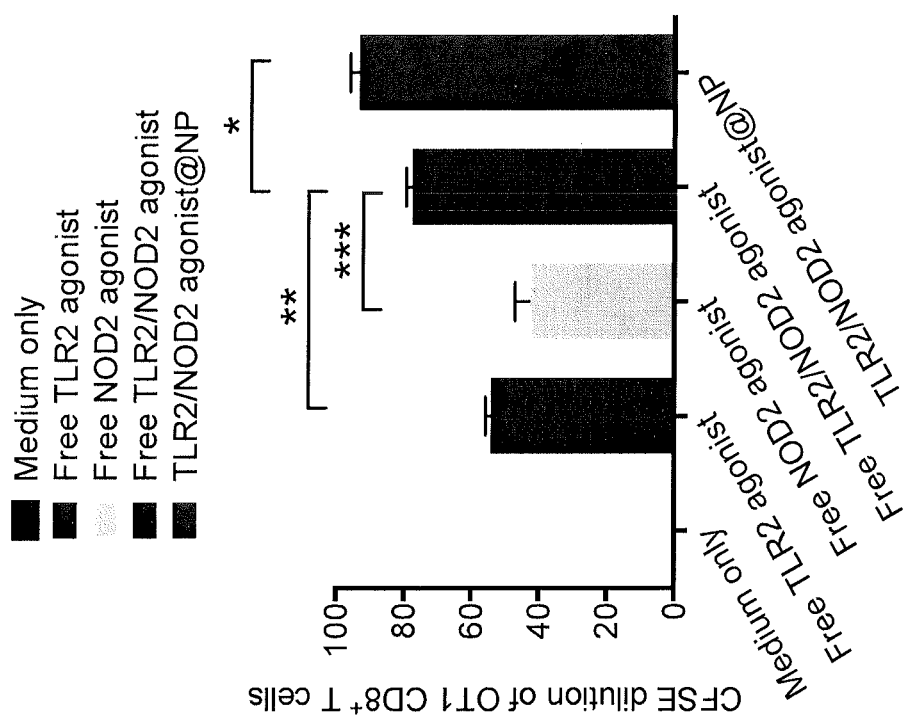

FIG. 16. Dendritic cell (DC) cell line (JAWSII) were incubated overnight with 2 μg/mL of OVA and maturation stimuli (agonist at 1 μg/mL) (or DC medium alone). DCs were washed 3 times and co-cultured with 30,000 CFSE-labeled OT-I CD8$^+$ T cells. Cells were collected after 6 days of co-culture. Extent of proliferation was quantified by determining the % of cells that had undergone division by determining % of viable CD8$^+$ T cells that had diluted CFSE.

Figure 17:
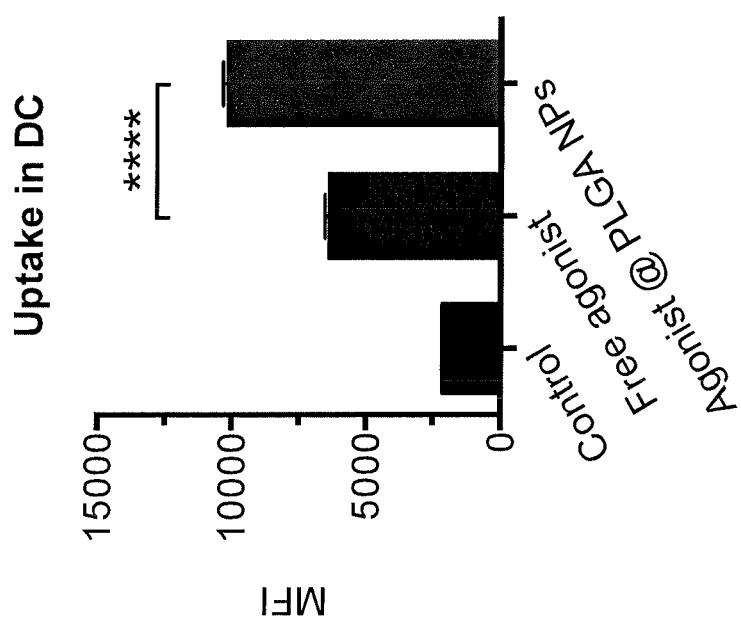

FIG. 17. Stimulatory PLGA NPs significantly improve the uptake of TLR2 and NOD2 agonists by dendritic cells. Rhodamine labeled TLR2 and NOD2 agonist or rhodamine labeled TLR2 and NOD2 agonists encapsulated stimulatory PLGA NPs were incubated with JAWSII dendritic cells at 37° C. for 4 hours. Cells were stained and uptake was quantified by flow cytometry using the mean fluorescence intensity (MFI) of rhodamine.

Figure 18:
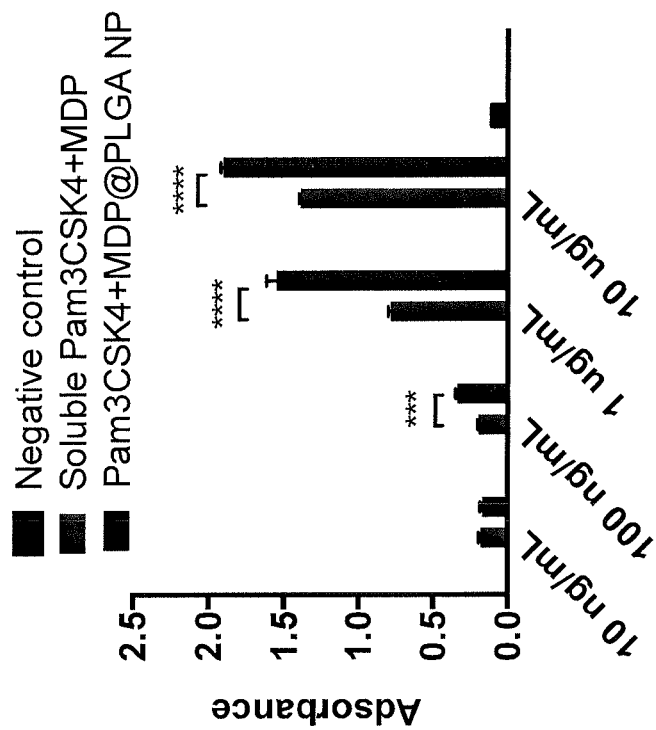

FIG. 18. Stimulatory PLGA NPs could enhance the activation of RAW macrophages bearing a NF-κB reporter as compared to soluble TLR2 and NOD2 agonists. TLR2 and NOD2 agonists containing stimulatory PLGA NPs or mixture of TLR2 and NOD2 were incubated for 24 hours with the InvivoGen HEK-BLUE™ murine TLR2 reporter cell line, a secreted embryonic alkaline phosphatase (SEAP) reporter system. SEAP levels were quantified by incubating supernatant with QUANTIBLUE™ substrate for 1 h and reading absorption at 620 nm.

Figure 19:
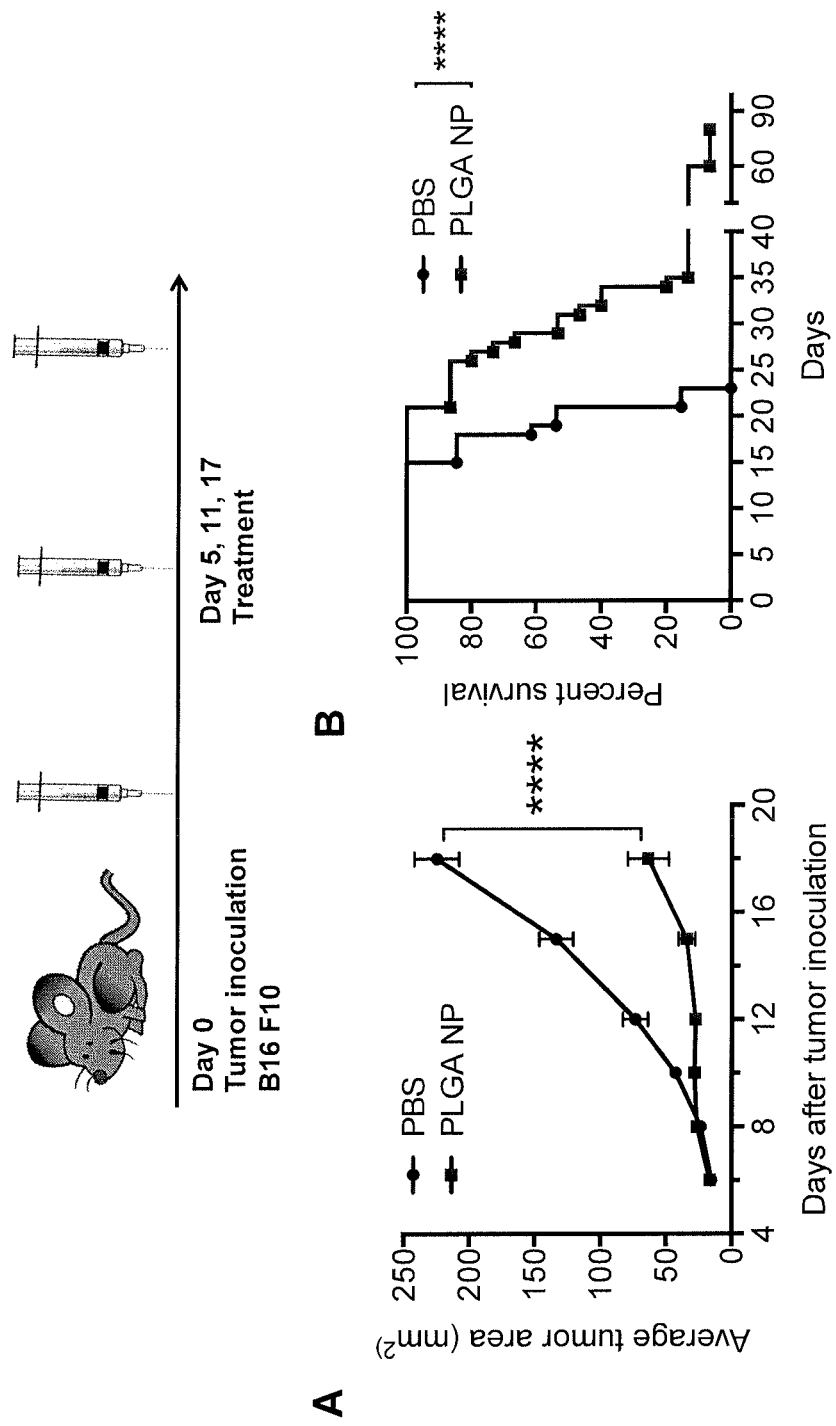

FIG. 19. Stimulatory PLGA NP suppresses the tumor growth, prolongs the overall survival in B16F0 melanoma model. (A) The average tumor growth curve of B16F10 melanoma treated with PBS or stimulatory PLGA NP (160 ng of IL-2, 10 μg of TLR2 agonist, 10 μg of NOD2 agonist, 20 μg of anti-CD28). (N=10). **, p<0.0001; , p<0.01; *, p<0.05 Data was analyzed by two-way ANOVA. (B) The percentage survival of mice bearing B16F10 melanoma after PBS and stimulatory PLGA NP treatments was monitored over time. **, p<0.0001; , p<0.01; * p<0.05 Data was analyzed by Log-rank (Mantel-Cox) test.

Figure 20:
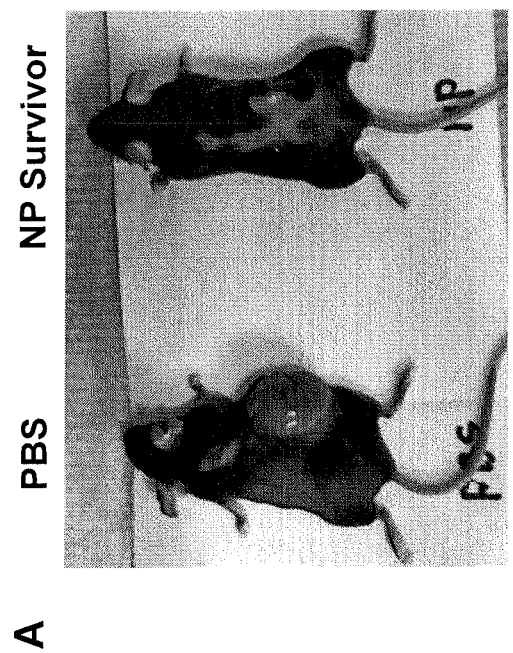
Figure 20:
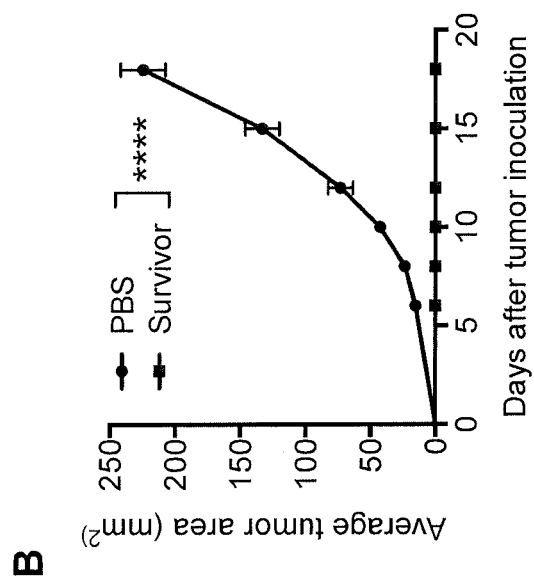

FIG. 20. Stimulatory PLGA NP establishes the protective memory in B16F10 tumor model. (A) The representative image of survivor mouse received the second tumor challenge (0.1M B16F10 cells). The photo was taken 17 days post second tumor inoculation. (B) The tumor growth curve of survivors bearing B16F10 received second tumor challenge on Day 70. **, p<0.0001; , p<0.01; * p<0.05 Data was analyzed by two-way ANOVA.

Figure 21:
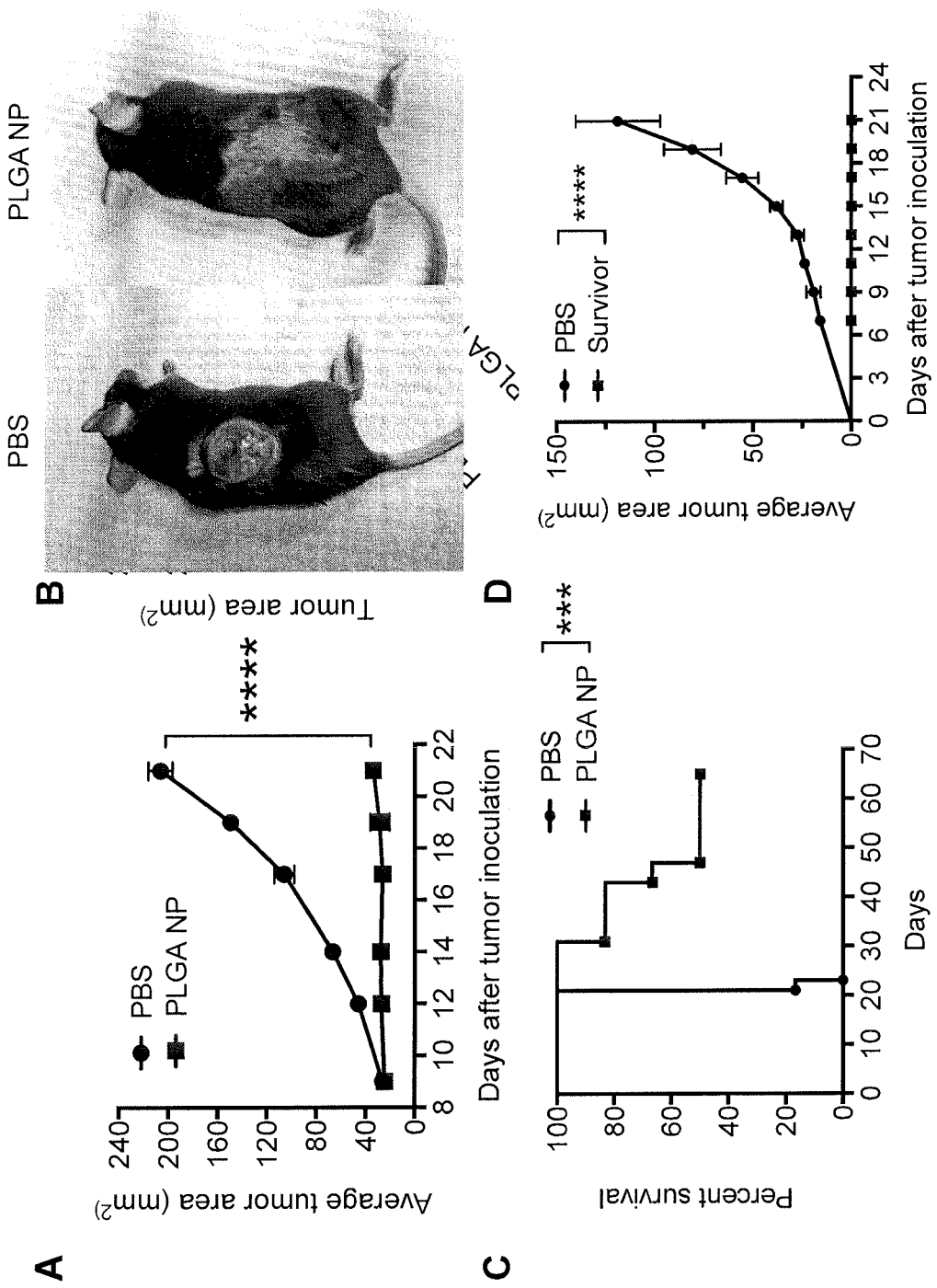

FIG. 21. Stimulatory PLGA NP suppresses the tumor growth, prolongs the overall survival and establishes the protective memory in MC38 tumor model. (A) The average tumor growth curve MC38 murine colon cancer treated with PBS or stimulatory PLGA NP (N=6). **, p<0.0001; , p<0.01; * p<0.05 Data was analyzed by two-way ANOVA. (B) The representative image of mice received the treatment of PBS or stimulatory PLGA NP on day 17. (C) The percentage survival of mice bearing MC38 after three times of treatment was monitored over time. **, p<0.0001; , p<0.01; * p<0.05 Data was analyzed by Log-rank (Mantel-Cox) test. (D) The tumor growth curve of survivors bearing MC38 received second tumor challenge on Day 70. **, p<0.0001; , p<0.01; * p<0.05 Data was analyzed by two-way ANOVA.

Figure 22:
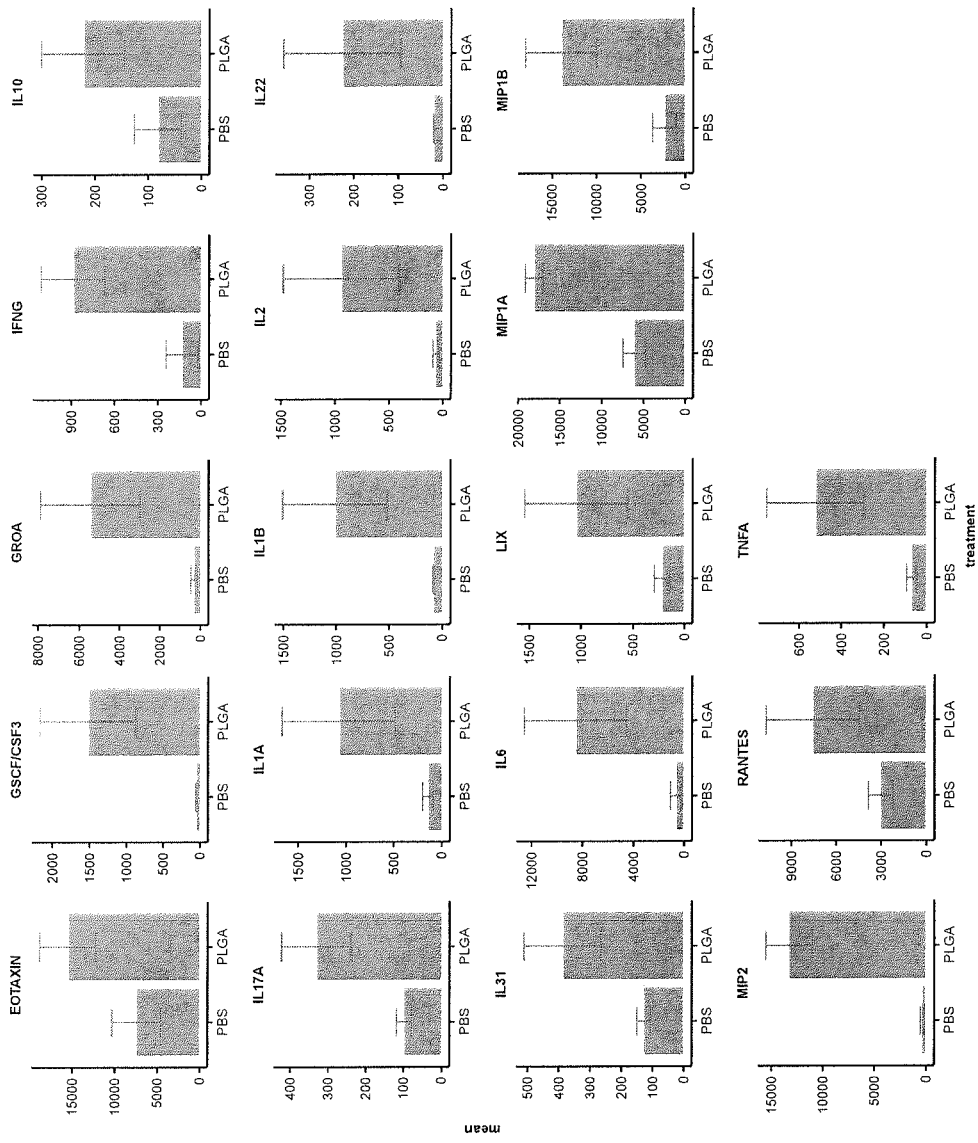

FIG. 22. Stimulatory PLGA NP remodels the tumor microenvironment of established B16F10 melanoma tumor by up-regulating a variety of pro-inflammatory cytokines expression (Y axis represents the mean fluorescence intensity). Data was collected 3 days after stimulatory PLGA NP treatment.

Figure 23:
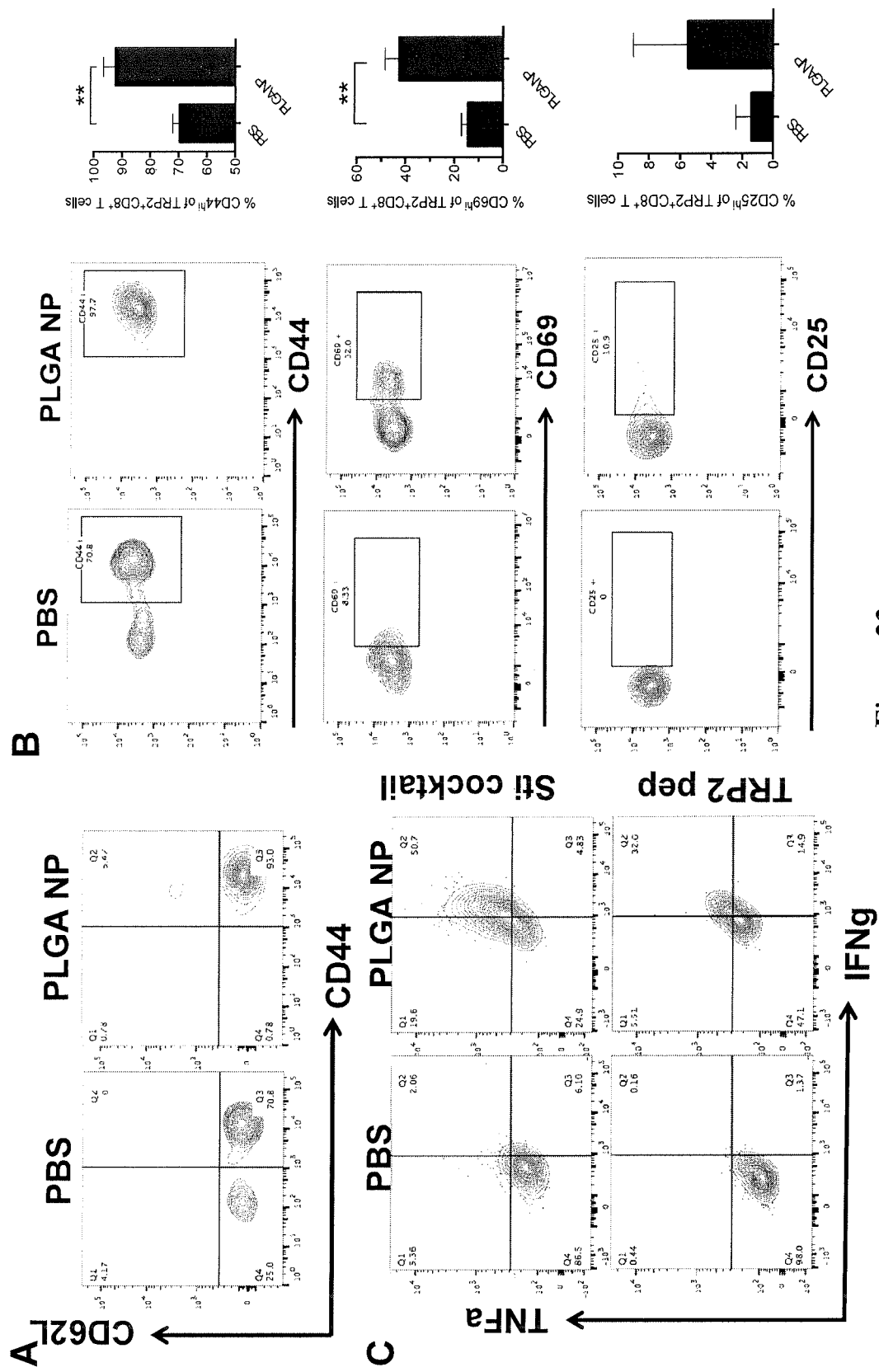

FIG. 23. Stimulatory PLGA NP induces potent endogenous self-specific CD8$^+$ T cell response in B16F10 melanoma model. (A) stimulatory PLGA NP drives self-specific (TRP2$^+$) T cell response strongly biased toward effector memory (CD44$^{hi}$CD62L$^{lo}$) populations in tumor. (B) The representative flow cytometry plot (left panel) and the corresponding quantification (right panel) of surface activation marker staining (CD44, CD69 and CD25) of self-specific TRP2$^+$ tumor infiltrating CD8$^+$ T cells from freshly isolated B16F10 melanoma. **, p<0.0001; , p<0.01; *p<0.05 Data was analyzed by student T test. (C) The representative flow cytometry plot of intracellular cytokine staining of tumor infiltrating CD8$^+$ T cells from B16F10 melanoma after ex vivo stimulation of cell stimulation cocktail (upper panel) or TRP2 peptide (bottom panel).

Figure 24:
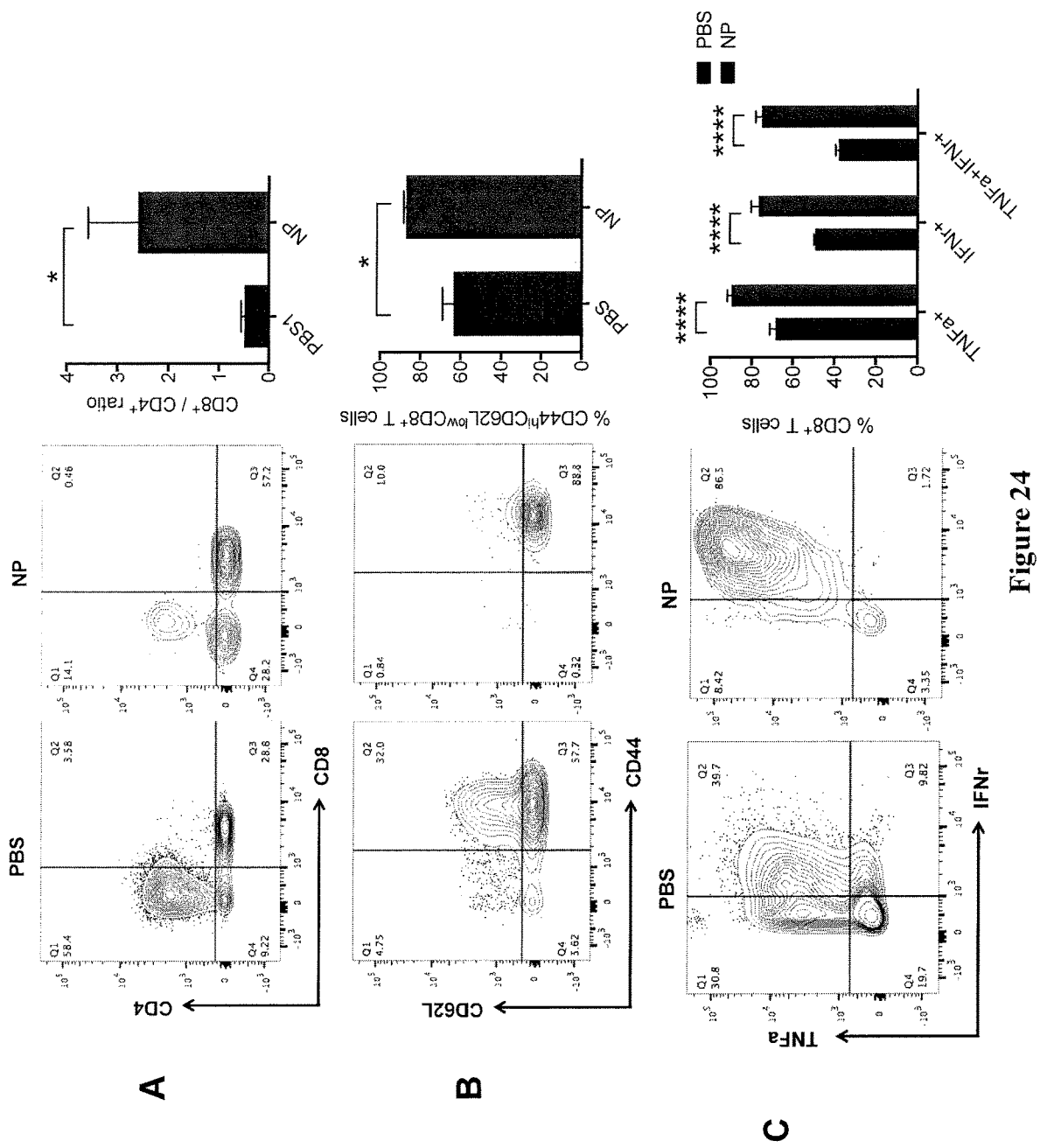

FIG. 24. Stimulatory PLGA NP elicits the potent T cell response in MC38 tumor model. (A) The frequency change of CD8$^+$ T cells and CD4$^+$ T cells. (B) The phenotype staining of freshly isolated tumor infiltrating CD8$^+$ T cells from MC38 colon cancer. (C) The intracellular cytokine staining of tumor infiltrating CD8$^+$ T cells from MC38 colon cancer after ex vivo stimulation by cell stimulation cocktail for 5 h. **, p<0.0001; , p<0.01; * p<0.05 Data was analyzed by student T test.

Figure 25:
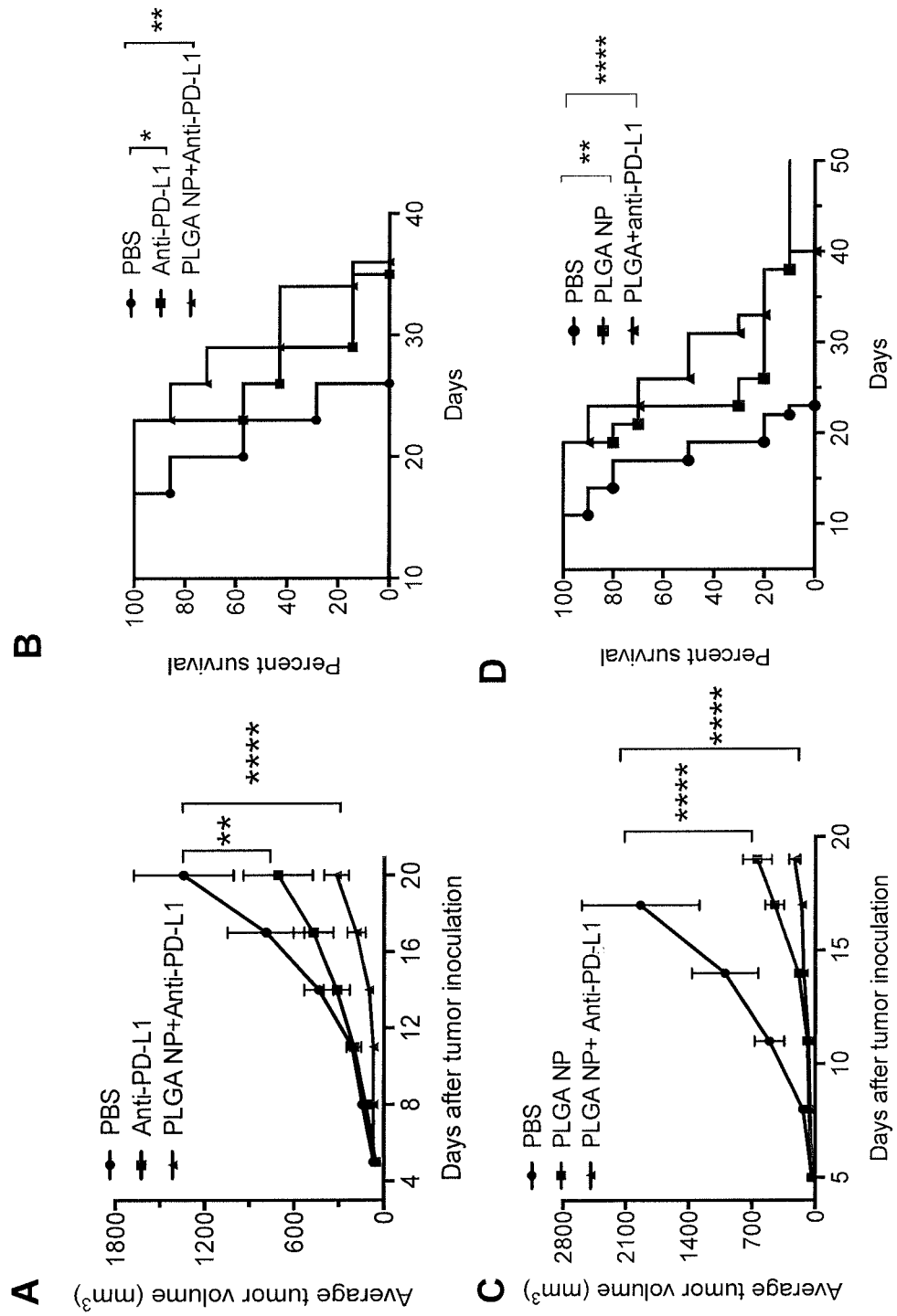

FIG. 25. Antitumor efficacy of the combination of stimulatory PLGA NP and anti-PD-L1 antibody (Ab) in murine B16F10 melanoma. (A) The average tumor growth curve of B16F10 melanoma treated with PBS, anti-PD-L1 and the combination of stimulatory PLGA NP and anti-PD-L1 Ab. **, p<0.0001; , p<0.01; * p<0.05 Data was analyzed by two-way ANOVA. (B) The percentage survival of mice after three treatments was monitored over time. **, p<0.0001; , p<0.01; * p<0.05 Data was analyzed by Log-rank (Mantel-Cox) test. (C) The average tumor growth curve of B16F10 melanoma treated with PBS, anti-PD-L1 and the combination of stimulatory PLGA NP and anti-PD-L1 Ab. **, p<0.0001; , p<0.01; * p<0.05 Data was analyzed by two-way ANOVA. (D) The percentage survival of mice after three treatments was monitored over time. **, p<0.0001; , p<0.01; * p<0.05 Data was analyzed by Log-rank (Mantel-Cox) test.

Figure 26:
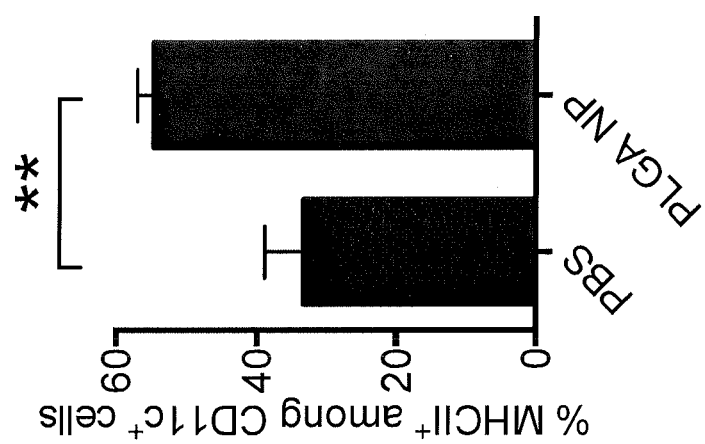

FIG. 26. Stimulatory PLGA NPs enhance the maturation of DC (CD11b$^+$CD11c$^+$) in tumor, characterized by up-regulation of MHC class II expression. **, p<0.0001; , p<0.01; * p<0.05. Data was analyzed by student T test.

Figure 27:
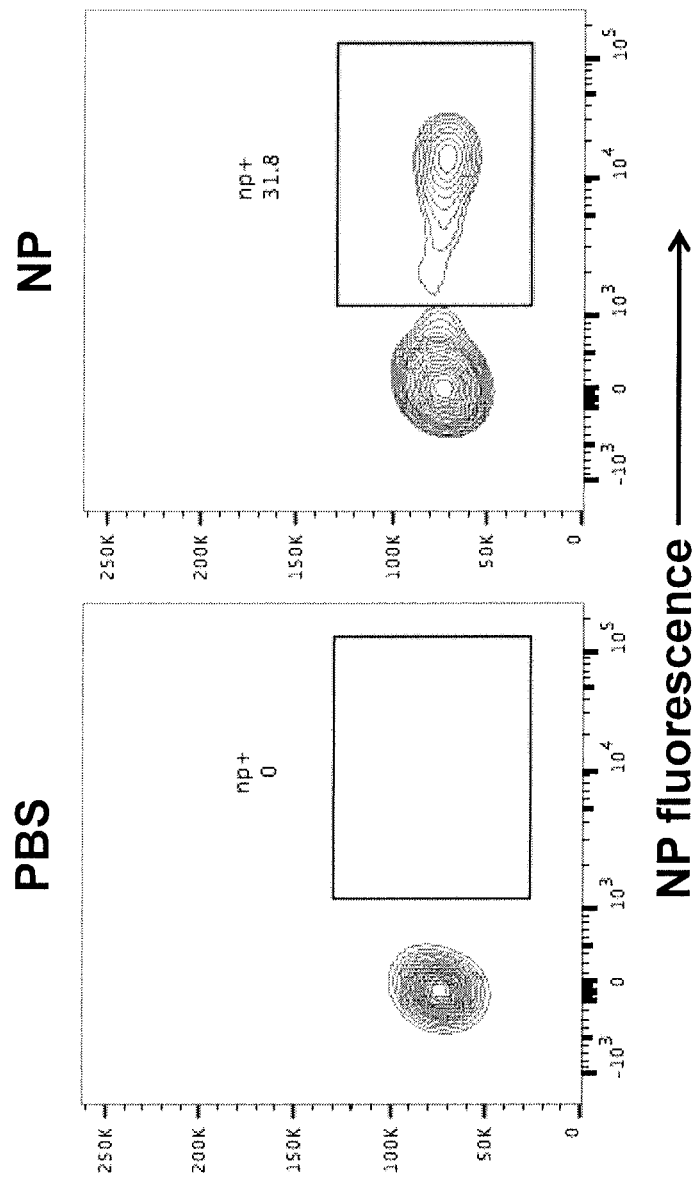

FIG. 27. Cellular uptake of fluorescently labeled stimulatory PLGA NPs in CD11b$^+$CD11c$^+$ dendritic cells. Cells were isolated and stained 24 h after intratumoral injection of stimulatory PLGA NPs.

Figure 28:
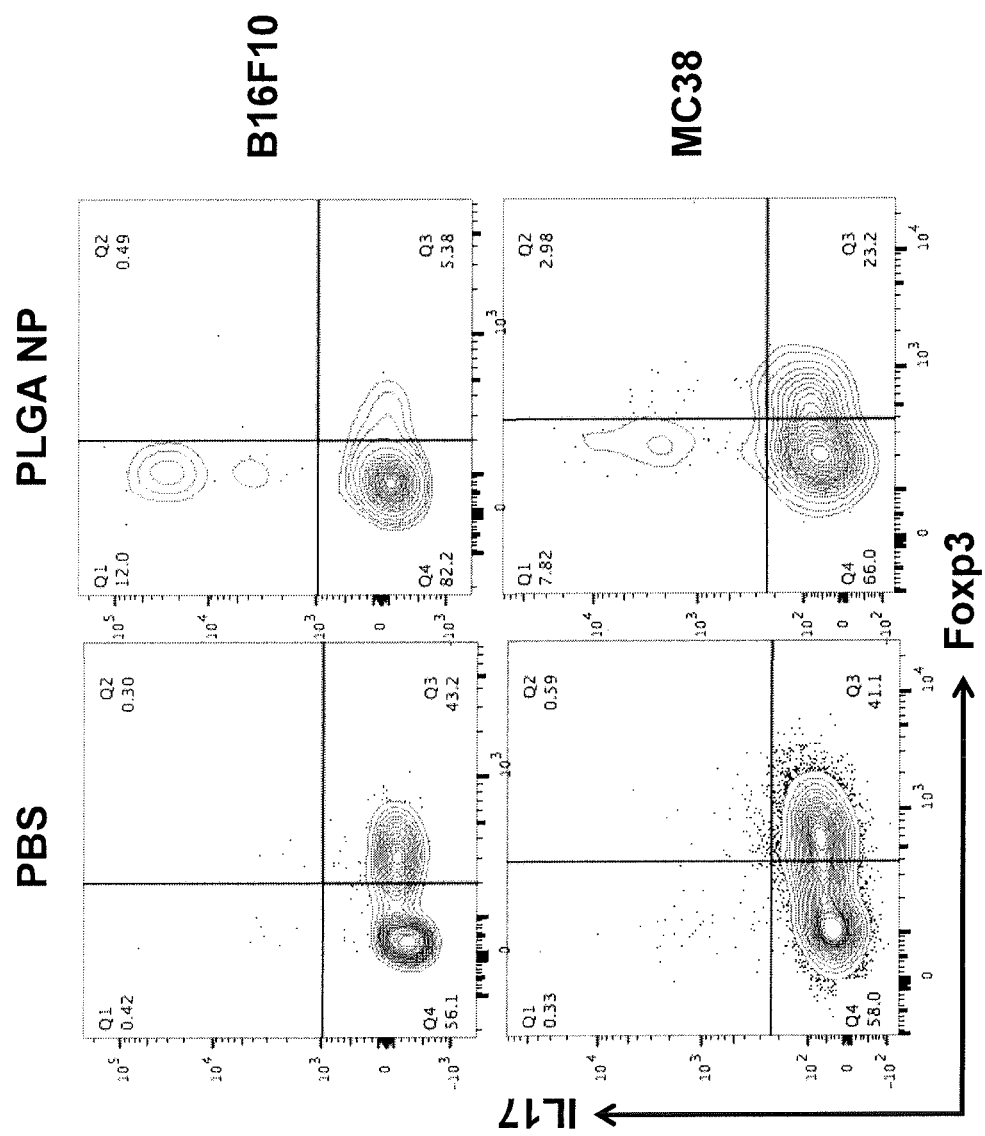

FIG. 28. Stimulatory PLGA NPs decreased frequencies of regulatory T cells (Treg CD4$^+$Foxp3$^+$ cells) and the increased frequencies of Th17 (CD4$^+$IL17$^+$) cells. The representative flow cytometry plot of tumor infiltrating CD4$^+$ T cells from B16F10 melanoma (upper) and MC38 (bottom) after ex vivo stimulation of cell stimulation cocktail for 5 h.

DETAILED DESCRIPTION OF THE EMBODIMENTS

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

"Measuring" or "measurement" in the context of the present teachings refers to determining the presence, absence, quantity, amount, or effective amount of a substance in a clinical or subject-derived sample, including the presence, absence, or concentration levels of such substances, and/or evaluating the values or categorization of a subject's clinical parameters based on a control. Measuring emission of light, either integrated total emission or detection of particles corresponding to rare cells or biological entities may be performed.

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

Immunostimulatory. As used herein the term immunostimulatory refers to compositions that increase the activity of immune cells, particularly compositions that increase the activity of T effector cells, including without limitation CD8+ cytotoxic T cells; and antigen-presenting dendritic cells. The polymeric nanoparticles described herein comprise immunostimulatory compounds, and the nanoparticles have been demonstrated to increase the anti-tumor efficacy of tumor infiltrating lymphocytes (TILs) present in a tumor microenvironment. After administration of the nanoparticles, CD8+ tumor infiltrating T cells also have increased expression of activation markers, e.g. CD25, CD44 and CD69. Immunostimulation may also refer to expansion of T cells expressing pro-inflammatory cytokines, and increased levels of pro-inflammatory cytokines in serum and a tumor microenvironment, for example as shown in FIGS. 13 and 22. The immunostimulatory compositions can decrease frequency or activity of suppressive immune cells, e.g. Foxp3+ regulatory T cells.

Immunostimulation may also refer to the effect a composition has on the stimulation of dendritic cells, for example where dendritic cells internalize nanoparticles, resulting in increased expression of maturation markers such as CD86, MHC class II antigens, etc.

Payload. Nanoparticles described herein comprise an encapsulated payload, where the term payload refers to one, two, three or more immunostimulatory agents contained within the nanoparticle, i.e. agents are enclosed within the nanoparticle. In some embodiments the encapsulated payload comprises at least one immunostimulatory compound. In some embodiments the encapsulated payload comprises two immunostimulatory compounds. In some embodiments the encapsulated payload comprises three immunostimulatory compounds. The immunostimulatory compound(s) may be selected from toll-like receptor (TLR) agonists, nucleotide-binding oligomerization domain 2 (NOD2) agonists, and cytokines. In some embodiments the at least one immunostimulatory compound is a TLR agonist. In some embodiments the TLR agonist is a TLR2 agonist. A combination of nanoparticles with differing payloads may be formulated for administration, e.g. a combination of two or more different species of nanoparticle, where one species of nanoparticle comprises a cytokine; one species comprises a TLR agonist; one species of nanoparticle comprises a NOD2 agonist, and the like.

Specific payload components are described in detail below.

The Toll-like receptors are type I transmembrane (TM) proteins that function as pattern recognition receptors (PRR)s that possess varying numbers of extracellular N-terminal leucine-rich repeat (LRR) motifs, followed by a cysteine-rich region, a TM domain, and an intracellular Toll/IL-1 R (TIR) motif. The LLR domain is important for ligand binding and associated signaling and is a common feature of PRRs. The TIR domain is important in protein-protein interactions and is typically associated with innate immunity. The TIR domain also unites a larger IL-1 R/TLR superfamily that is composed of three subgroups.

TLR1 and TLR2 can heterodimerize to recognize a variety of bacterial lipid structures and cell wall components, such as triacylated lipoproteins, lipoteichoic acid, and β-glucans. TLR2 also heterodimerizes with TLR6 to bind diacylated lipopeptides. Additionally, TLR2 can bind various endogenous DAMPs, such as HSPs, HMGB1, uric acid, fibronectin, and other extracellular matrix proteins.

TLR agonist. TLR agonists activate TLRs, including for the purposes of the present invention TLR2. TLR agonists are currently under investigation as vaccine adjuvants in anticancer therapies for their ability to activate immune cells and promote inflammation. Examples of TLR agonists include pathogen-associated molecular patterns (PAMPs) and mimetics thereof. These microbial molecular markers may be composed of proteins, carbohydrates, lipids, nucleic acids and/or combinations thereof, and may be located internally or externally, as known in the art. Examples include, without limitation, lipopolysaccharide (LPS), zymosan, peptidoglycans, flagellin, synthetic TLR2 agonist Pam3cys, Pam3CSK4, MALP-2, triacylated lipoproteins, lipoteichoic acid, peptidoglycans, diacylated lipopeptides, and the like. The TLR2 ligand may include one or more of lipoteichoic acid (LTA), a synthetic tripalmitoylated lipopeptide ($PAM_3CSK_4$), zymosan, a lipoglycan such as lipoarabinomannan or lipomannan, a peptidoglycan, diacylated lipoprotein MALP-2, synthetic diacylated lipoprotein FSL-1, heat shock protein HSP60, heat shock protein HSP70, heat shock protein HSP96 or high-mobility-group protein 1 (HMG-1).

In certain embodiments, the TLR agonist is a TLR2 agonist. In some embodiments the TLR2 agonist is $Pam_3CSK_4$ which is a commercially available synthetic tripalmitoylated lipoprotein that mimics the acylated amino terminus of bacterial LPs. $Pam_3CSK_4$ is a potent activator of the proinflammatory transcription factor NF-κB.

The engagement of TLR1-TLR2 on CD8+ CTLs dramatically increases the production of IFN-γ, TNF-α, and IL-2 production. TLR2 engagement can also enhance the production of granzyme B and perforin, which are two of the major cytolytic molecules secreted by cytotoxic CD8+ T cells. Immune suppression and T cell tolerance represent major obstacles for achieving effective and durable antitumor responses. Among the various cellular mechanisms that hinder a productive antitumor response are those mediated by $T_{Regs}$. The immunosuppressive activity of these cells is, in part, mediated by the production of IL-10 and TGF-β, which severely limit the cytolytic activity of tumor-specific CD8+ T cells. TLR2 stimulation directly on $T_{Regs}$ has been shown to reduce their suppressive function. TLR1-TLR2 activation on CD8+ T cells may also reduce the TCR activation threshold and facilitate the generation of memory cells in response to a weak TCR signal.

The dose of TLR agonist that is effective in the methods of the invention is a dose that increases the efficiency of T cell response against tumor antigens, relative to the same population in the absence of the TLR agonist. An effective dose may be up to about 10 μg/kg body weight, up to about 50 μg/kg, up to about 100 μg/kg, up to about 250 μg/kg, up to about 500 μg/kg, up to about 750 μg/kg, up to about 1 mg/kg, up to about 2.5 mg/kg, up to about 5 mg/kg, up to about 10 mg/kg or more, administered in a nanoparticle formulation.

Nod2 agonist. Nucleotide-binding oligomerization domain 2 (NOD2) is an intracellular pattern recognition receptor that senses bacterial peptidoglycan (PGN)-conserved motifs in cytosol and stimulates host immune response. Stimulation of NOD2 by its ligand (muramyl dipeptide) activates pro-inflammatory pathways such as nuclear factor κB (NF-κB), mitogen-activated protein kinases (MAPKs), and Caspase-1. Because the ligand of Nod2 is conserved in both gram-positive and gram-negative bacteria, NOD2 detects a wide variety of microorganisms.

Agonists of NOD2 include, without limitation, MDP (MurNAc-L-Ala-D-isoGln, also known as muramyl dipeptide), which is the minimal bioactive peptidoglycan motif common to all bacteria and the essential structure required for adjuvant activity in vaccines. Derivatives of MDP also find use as agonists, and include, without limitation, L18-MDP and N-glycolyl-MDP, which display strong adjuvant activity. Other NOD2 activators include MurNAc-L-Ala-γ-D-Glu-L-Lys, also called MtriLYS); mirabutide, muramyl tripeptide phosphatidylethanolamine (MTP-PE), and liposome encapsulated muramyl tripeptide-phosphatidylethanolamine (L-MTP-PE). MTP-PE (Mifamurtide) is clinically approved for treatment of osteosarcoma.

In certain embodiments the NOD2 agonist is a derivative of muramyl dipeptide. In some embodiments the NOD2 agonist is the commercially available MDP derivative L18-MDP, a 6-O-acyl derivative with a stearoyl fatty acid.

An effective dose may be up to about 10 (g/kg body weight, up to about 50 μg/kg, up to about 100 μg/kg, up to about 250 μg/kg, up to about 500 μg/kg, up to about 750 μg/kg, up to about 1 mg/kg, up to about 2.5 mg/kg, up to about 5 mg/kg, up to about 10 mg/kg or more, administered in a nanoparticle formulation.

Therapeutic antibody. As used herein, a therapeutic antibody is an immunostimulatory antibody, e.g. an antibody conjugated to the polymeric nanoparticle. The therapeutic antibody stimulates T cell activity, e.g. by increasing activity of effector T cells. The therapeutic antibody may specifically bind to a molecule present on the surface of T cells. The therapeutic antibody may specifically bind to and activate a molecule present on the surface of T cells. The therapeutic antibody may specifically bind to and activate a component of the TCR or a co-stimulatory protein. A component of the TCR may include, for example, CD3.

In some embodiments, the therapeutic antibody is an agonist antibody that binds to and activates a co-stimulatory protein, which co-stimulatory proteins include, without limitation, CD28, CD27, inducible co-stimulator (ICOS), OX40, glucocorticoid-induced TNFR family related gene (GITR), CD137 (4-1BB), and T-cell immunoglobulin and mucin domain 1 (TIM-1). In some embodiments the therapeutic antibody is an anti-CD28 agonist antibody.

CD28 is a costimulatory molecule expressed on T lymphocytes. CD28 binds B7 molecules to provide a costimulatory signal that is important for sustaining T-lymphocyte activation, proliferation and a pro-inflammatory response. ICOSL/CD28 interaction may be involved in the costimulation of human T cells' primary responses to allogeneic antigens and memory recall responses.

Antibodies directed against CD28 can be divided into two classes based on their target epitope and their stimulatory activity on T lymphocytes. "Superagonistic anti-CD28 antibodies" refer to a nonphysiological engagement of CD28 by its basolateral domain resulting in a polyclonal activation of T lymphocytes even in the absence of TCR stimulation. Such superagonistic antibodies are generally not used in the formulations and methods of the present invention, i.e. the nanoparticles comprise a non-superagonistic anti-CD28 antibody.

Conventional anti-CD28 antibodies cross-link CD28 by any epitope lying outside the basolateral domain and costimulate T cells only in synergy with a TCR stimulation. Monovalent fragments from conventional anti-CD28 antibodies cannot costimulate T-cell activation even with TCR signals, presumably because they cannot multimerize CD28. Anti-human CD28 antibodies can be generated, or selected from those known in the art and commercially available, and may include, without limitation, lumretuzumab (TAB-H47); (TAB-065LC); HuTN228 (TAB-069LC); lulizumab pegol (TAB-H46); FK734, etc. See, for example, Zheng et al. (2009) Cytotechnology 60(1-3):85-94; Shiao et al. (2007) Transplantation 83(3):304-313.

An effective dose of the therapeutic antibody may be up to about 50 μg/kg, up to about 100 μg/kg, up to about 250 μg/kg, up to about 500 μg/kg, up to about 750 μg/kg, up to about 1 mg/kg, up to about 2.5 mg/kg, up to about 5 mg/kg, up to about 10 mg/kg, up to about 15 mg/kg, up to about 20 mg/kg, up to about 25 mg/kg or more, administered in a nanoparticle formulation.

Cytokine. Cytokines of interest for the formulations herein are proteins, which include chemokines, interferons, interleukins, lymphokines, and tumor necrosis factors, that act to activate immune cells. Of interest are pro-inflammatory cytokines, sometimes referred to as type 1 cytokines, which stimulate T effector cell activity. The pro-inflammatory cytokine may include, without limitation, one or a combination of interleukin 2 (IL-2), interferon gamma (IFNγ), tumor necrosis factor alpha (TNFα), interleukin 6 (IL-6), IL-7, interleukin 12 (IL-12), and interleukin 15 (IL-15), or analogs, derivatives and mimetics thereof.

In some embodiments a pro-inflammatory cytokine is IL-2. Interleukin 2 (IL-2) is a plunpotent cytokine produced primarily by activated $CD4^+$ T cells and plays a crucial role in producing a normal immune response. IL-2 promotes proliferation and expansion of activated T lymphocytes, potentiates B cell growth, and activates monocytes and natural killer cells. It was by virtue of these activities that IL-2 was tested and is used as an approved treatment of cancer in humans (aldesleukin, Proleukin®). In eukaryotic cells human IL-2 is synthesized as a precursor polypeptide of 153 amino acids, from which 20 amino acids are removed to generate mature secreted IL-2. Interking is a recombinant IL-2 with a seine at residue 125. Other variants include teceleukin, with a methionine added at the N-terminus, and bioleukin, with a methionine added at the N-terminus and residue 125 replaced with alanine.

As used herein, "IL-2" refers to the native, or wild-type human IL-2, and biologically active variants thereof, for example as described above. Mature human IL-2 occurs as a 133 amino acid sequence (less the signal peptide, consisting of an additional 20 N-terminal amino acids), as described in Fujita, et. al, PNAS USA, 80, 7437-7441 (1983). The amino acid sequence of human IL-2 is found in Genbank under accession locator NP_000577.2.

An effective dose may be up to about 1 μg/kg body weight, up to about 2.5 μg/kg, up to about 5 μg/kg, up to about 10 μg/kg, up to about 25 μg/kg, up to about 50 μg/kg, up to about 100 μg/kg, up to about 250 μg/kg, up to about 500 μg/kg, up to about 750 μg/kg, up to about 1 mg/kg, up to about 2.5 mg/kg, up to about 5 mg/kg, up to about 10 mg/kg or more, administered in a nanoparticle formulation.

Immunoregulatory agent. In some embodiments an effective dose of an immunoregulatory modulating agent is administered in combination with an effective dose of the polymeric nanoparticle. The immunoregulatory modulating agent may be conjugated to the nanoparticle or may not be conjugated to the nanoparticle. In some embodiments the immunoregulatory agent is an antibody that binds to and inhibits an immune, e.g. T cell, checkpoint protein, and is not conjugated to the nanoparticle but is administered in a combination therapy.

Immune checkpoint proteins are immune inhibitory molecules that act to decrease immune responsiveness toward a target cell, particularly against a tumor cell in the methods of the invention. Endogenous responses to tumors by T cells can be dysregulated by tumor cells activating immune checkpoints (immune inhibitory proteins) and inhibiting co-stimulatory receptors (immune activating proteins). The class of therapeutic agents referred to in the art as "immune checkpoint inhibitors" reverses the inhibition of immune responses through administering antagonists of inhibitory signals.

An effective dose of an antibody that binds to an inhibits an immune checkpoint protein may be up to about 50 µg/kg, up to about 100 µg/kg, up to about 250 µg/kg, up to about 500 µg/kg, up to about 750 µg/kg, up to about 1 mg/kg, up to about 2.5 mg/kg, up to about 5 mg/kg, up to about 10 mg/kg, up to about 15 mg/kg, up to about 20 mg/kg, up to about 25 mg/kg or more.

The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and that combinatorial strategies can be utilized.

CTLA4 is expressed exclusively on T cells where it primarily regulates the amplitude of the early stages of T cell activation. CTLA4 counteracts the activity of the T cell co-stimulatory receptor, CD28. Two fully humanized CTLA4 antibodies, ipilimumab and tremelimumab, are in clinical testing and use.

The major role of PD1 is to limit the activity of T cells in peripheral tissues at the time of an inflammatory response to infection and to limit autoimmunity. PD1 expression is induced when T cells become activated. When engaged by one of its ligands, PD1 inhibits kinases that are involved in T cell activation. PD1 is highly expressed on $T_{Reg}$, cells, where it may enhance their proliferation in the presence of ligand. Because many tumors are highly infiltrated with $T_{Reg}$ cells, blockade of the PD1 pathway may also enhance antitumor immune responses by diminishing the number and/or suppressive activity of intratumoral $T_{Reg}$ cells. PD-1 inhibitors in clinical use include Atezolizumab, Avelumab and Durvalumab.

The two ligands for PD1 are PD1 ligand 1 (PDL1; also known as B7-H1 and CD274) and PDL2 (also known as B7-DC and CD273). The PD1 ligands are commonly upregulated on the tumor cell surface from many different human tumors. On cells from solid tumors, the major PD1 ligand that is expressed is PDL1. PDL1 is expressed on cancer cells and through binding to it's receptor PD1 on T cells it inhibits T cell activation/function. Therefore, PD1 and PDL1 blocking agents can overcome this inhibitory signaling and maintain or restore anti-tumor T cell function. PDL1 inhibitors in clinical use include Nivolumab and Pembrolizumab.

Other checkpoint proteins may include lymphocyte activation gene 3 (LAG3; also known as CD223), 2B4 (also known as CD244), B and T lymphocyte attenuator (BTLA; also known as CD272), T cell membrane protein 3 (TIM3; also known as HAVcr2), which each been associated with the inhibition of lymphocyte activity and in some cases the induction of lymphocyte anergy.

LAG3 is a CD4 homolog that enhances the function of $T_{Reg}$ cells. LAG3 also inhibits CD8$^+$ effector T cell functions independently of its role on $T_{Reg}$ cells. The only known ligand for LAG3 is MHC class II molecules, which are expressed on tumor-infiltrating macrophages and dendritic cells. LAG3 is one of various immune-checkpoint receptors that are coordinately upregulated on both $T_{Reg}$ cells and anergic T cells, and simultaneous blockade of these receptors can result in enhanced reversal of this anergic state relative to blockade of one receptor alone. In particular, PD1 and LAG3 are commonly co-expressed on anergic or exhausted T cells. Dual blockade of LAG3 and PD1 synergistically reversed anergy among tumor-specific CD8$^+$ T cells and virus-specific CD8$^+$ T cells in the setting of chronic infection. LAG3 blocking agents can overcome this inhibitory signaling and maintain or restore anti-tumor T cell function.

TIM3 inhibits T helper 1 ($T_H 1$) cell responses, and TIM3 antibodies enhance anti-tumor immunity. TIM3 has also been reported to be co-expressed with PD1 on tumor-specific CD8$^+$ T cells. Tim3 blocking agents can overcome this inhibitory signaling and maintain or restore anti-tumor T cell function.

BTLA is an inhibitory receptor on T cells that interacts with TNFRSF14. BTLA$^{hi}$ T cells are inhibited in the presence of its ligand. The system of interacting molecules is complex: CD160 (an immunoglobulin superfamily member) and LIGHT (also known as TNFSF14), mediate inhibitory and co-stimulatory activity, respectively. Signaling can be bidirectional, depending on the specific combination of interactions. Dual blockade of BTLA and PD1 enhances antitumor immunity.

Tumor antigens are antigens that are specifically or selectively expressed on cancer cells. Included are purified proteins or other biomolecules, killed cancer cells, extracts of cancer cells, etc. In some embodiments a purified preparation of a tumor antigen is administered, which may include, without limitation, one or more of the following antigens:

| | |
|---|---|
| TAG-72 | Prostate carcinoma |
| HPV E6, E7 | Cervical carcinoma |
| BING-4 | Melanoma |
| Calcium-activated chloride channel 2 | Lung carcinoma |
| Cyclin-B$_1$ | Multi |
| 9D7 | RCC |
| Ep-CAM | Breast carcinoma |
| EphA3 | Multi |
| Her2/neu | Multi |
| Telomerase | Multi |
| Mesothelin | Ductal pancreatic carcinoma |
| SAP-1 | Colorectal carcinoma |
| Survivin | Multi |
| BAGE family | Multi |
| CAGE family | Multi |
| GAGE family | Multi |
| MAGE family | Multi |
| SAGE family | Multi |
| XAGE family | Multi |
| NY-ESO-1/LAGE-1 | Multi |
| PRAME | Multi |
| SSX-2 | Melanoma, Multi |
| Melan-A/MART-1 | Melanoma |
| Gp100/pmel17 | Melanoma |
| Tyrosinase | Melanoma |
| TRP-1/-2 | Melanoma |
| P. polypeptide | Melanoma |
| MC1R | Melanoma |
| Prostate-pecific antigen | Prostate |
| β-catenin | Melanoma, Prostate, HCC |
| BRCA1/2 | Breast, ovarian carcinoma |
| CDK4 | Multi |
| CML66 | CML |
| Fibronectin | Multi |
| MART-2 | Melanoma |
| p53 | Multi |
| Ras | Multi |
| TGF-βRII | Colorectal carcinoma |
| MUC1 | Ductal carcinoma, RCC |
| Ig, TCR | B, T leukemia, lymphoma, myeloma |

In those embodiments where a purified tumor antigen is administered in combination with the subject nanoparticles, the effective dose may be up to about 50 µg/kg, up to about 100 µg/kg, up to about 250 µg/kg, up to about 500 µg/kg, up to about 750 µg/kg, up to about 1 mg/kg, up to about 2.5 mg/kg, up to about 5 mg/kg, up to about 10 mg/kg, up to about 15 mg/kg, up to about 20 mg/kg, up to about 25 mg/kg or more. The antigen may be administered as a free protein, i.e. not encapsulated or formulated within the nanoparticle itself.

Non-functional T cells. Various pathways can lead to T cell states in which the cells are non-functional in their response to antigenic stimulation. T cell anergy is an induced hyporesponsive state with low IL-2 production or incomplete activation. Anergy may results from T cells being stimulated with antigen in the presence of low co-stimulatory and/or high co-inhibitory signaling. These cells are unresponsive to subsequent activating conditions with limited IL-2 expression. Effector T cells that have lost their effector functions, including effector cytokine expression due to repeated stimulation are sometimes referred to as exhausted T cells. These non-functional T cells can express in different degrees inhibitory molecules including PD-1, Tim-3, LAG-3, 2B4, CD160, and KLGR-1.

Antigen specific, T cell-intrinsic dysfunction is an important feature in tumor microenvironments. Tumor induced T cell anergy or exhaustion may be an immune evasion mechanisms in patients with cancer.

The term "polypeptide," "peptide," "oligopeptide," and "protein," are used interchangeably herein, and refer to a polymeric form of amino acids of any length, which can include coded and non-coded amino acids, chemically, or biochemically modified or derivatized amino acids, and polypeptides having modified peptide backbones.

As used herein, the terms "purified" and "isolated" when used in the context of a polypeptide that is substantially free of contaminating materials from the material from which it was obtained, e.g. cellular materials, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide that is chemically synthesized refers to a polypeptide which is substantially free of chemical precursors or other chemicals which are involved in the syntheses of the polypeptide.

Polypeptides may be isolated and purified in accordance with conventional methods of recombinant synthesis or cell free protein synthesis. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention.

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

"In combination with", "combination therapy" and "combination products" refer, in certain embodiments, to the concurrent administration to a patient of the agents described herein. When administered in combination, each component can be administered at the same time or sequentially in any order at different points in time. Thus, each component can be administered separately but sufficiently closely in time so as to provide the desired therapeutic effect.

"Concomitant administration" of active agents in the methods of the invention means administration with the reagents at such time that the agents will have a therapeutic effect at the same time. Such concomitant administration may involve concurrent (i.e. at the same time), prior, or subsequent administration of the agents. A person of ordinary skill in the art would have no difficulty determining the appropriate timing, sequence and dosages of administration for particular drugs and compositions of the present invention.

As used herein, endpoints for treatment will be given a meaning as known in the art and as used by the Food and Drug Administration.

Overall survival is defined as the time from randomization until death from any cause, and is measured in the intent-to-treat population. Survival is considered the most reliable cancer endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased overall survival of patients.

Endpoints that are based on tumor assessments include DFS, ORR, TTP, PFS, and time-to-treatment failure (TTF). The collection and analysis of data on these time-dependent endpoints are based on indirect assessments, calculations, and estimates (e.g., tumor measurements). Disease-Free Survival (DFS) is defined as the time from randomization until recurrence of tumor or death from any cause. The most frequent use of this endpoint is in the adjuvant setting after definitive surgery or radiotherapy. DFS also can be an important endpoint when a large percentage of patients achieve complete responses with chemotherapy.

Objective Response Rate. ORR is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study.

Time to Progression and Progression-Free Survival. TTP and PFS have served as primary endpoints for drug approval. TTP is defined as the time from randomization until objective tumor progression; TTP does not include deaths. PFS is defined as the time from randomization until objective tumor progression or death. The precise definition of tumor progression is important and should be carefully detailed in the protocol.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

Nanoparticles

Polymer-encapsulated or conjugated drugs provide enhanced activity by protecting agents from degradation, targeting delivery to the desired site, ensuring combined agents are delivered, etc. The nanoparticle formulations provide for a longer biological half-life and improved efficacy with reduced systemic side effects. Polymers of interest are biodegradable polymers, including without limitation lactic acid polymers (PLA), glycolic acid polymers (PLG) and poly(lactic-co-glycolic acid) (PLGA). Active agents, such as a cytokine, TLR2 agonist and NOD2 agonist can be encapsulated in the nanoparticles. Additional agents, e.g. therapeutic antibodies, can be conjugated to the surface of the nanoparticles.

Oil-water (single) or water-oil-water (double) emulsion is one method by which polymers can be used to encapsulate active in micro- or nano-scale form. The polymer is dissolved into an organic phase (oil) that is emulsified with a surfactant or stabilizer (water). Hydrophobic drugs are added directly to the oil phase, whereas hydrophilic drugs (water) may be first emulsified with the polymer solution prior to formation of particles. High intensity sonication bursts facilitate the formation of small polymer droplets. The resulting emulsion is added to a larger aqueous phase and stirred for several hours, which allows the solvent to evaporate. Hardened nanoparticles are collected and washed by centrifugation.

The concentration of polymer will usually be at least about 0.01 mg/ml, more usually at least about 0.1 mg/ml, at least about 1 mg/ml, and not more than about 100 mg/ml, usually not more than about 50 mg/ml. The ratio of active agents to polymer as a weight percent will vary, from around about 1:1000; 1:500; 1:100, 1:50; 1:10; 1:5, and the like.

Solvents of interest are organic solvents, including, without limitation, dichloromethane (DCM), chloroform (CHF), tetrahydrofuran (THF), ethyl acetate, etc. The solvent solution with nucleic acid and polymer is dropped or injected at a set flow rate into a vessel filled with a miscible non-solvent. Flow rate may be optimized for each nucleic acid/polymer/solvent system. The selection is based on the desired yield and particle size. Miscible non-solvents for nanoprecipitation include, without limitation, ethanol, methanol, butanol etc.

Generally a temperature selected to maintain the stability of the proteins, and is usually not more than about 100° C., more usually not more than about 80° C., and may be not more than about 40° C., 30° C., or 20° C. It is desirable to keep the temperature below the glass transition temperature of the polymer, which typically ranges from 45-65° C., e.g. for PLGA. Therefore in some embodiments a temperature of around about 40° C. is used to advantage.

The nanoparticles may have a controlled size, as appropriate for optimization of delivery of the biologically active agents. Usually the particle will have a diameter of from about 50 nm, from about 100 nm, up to about 250 nm, up to about 500 nm, up to about 1 µm, up to about 2.5 µm, up to about 5 µm, and not more than about 10 µm in diameter. In some embodiments the nanoparticle size is from about 100 nm to about 5 µm in diameter, for example from about 100 nm to about 300 nm, from about 300 nm to about 2 µm, and the like. The nanoparticle optionally has a defined size range, which may be substantially homogeneous, where the variability may not be more than 100%, 50%, or 10% of the diameter. The sizes of particles can be altering by varying parameters, including the payload, the hydrophobicity of polymer, the type of organic solvent, organic solvent volume, solvent to polymer ratio, emulsifier, sonication intensity, centrifugation speed and time, and the like. See, for example, McCall, R. L., Sirianni, R. W. PLGA Nanoparticles Formed by Single- or Double-emulsion with Vitamin E-TPGS. *J. Vis. Exp.* (82), e51015, doi:10.3791/51015 (2013).

Chemical groups that find use in linking surface active agents, e.g. therapeutic antibodies which include, without limitation, an agonist of a T cell costimulatory protein such as anti-CD28 antibody, may utilize any suitable linker. Illustrative entities include: trioctylphosphine oxide, mercaptopropyltris(methyloxy)silane, aminopropyltris(methyloxy)silane, tetramethylammonium hydroxide, tetramethylammonium hydroxide pentahydrate, (trihydroxysilyl)propyl methylphosphonate, chlorotrimethylsilane, mercaptopropionic acid, 4-(dimethylamino)pridine, 5,5'-dithiobis(2-nitrobenzoic acid), azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-.gamma.-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraidehyde, NHS-PEG-MAL; succinimidyl 4-[N-maleimidomethyl]cyclohexane-1-carboxylate; 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC). Chemical groups that find use as couplings include amide (amine plus carboxylic acid), ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), hydrazide (aromatic hydrazide plus aromatic aldehyde) and the like, as known in the art. Maleimide linkage to protein sulfhydryl groups is of particular interest.

The nanoparticle may comprise a coating of any biologically compatible polymer. Some examples of biodegradable polymers useful as coating include hydroxyaliphatic carboxylic acids, either homo- or copolymers, such as poly(lactic acid), poly(glycolic acid), Poly(dl-lactide/glycolide, poly (ethylene glycol); polysaccharides, e.g. lectins, glycosaminoglycans, e.g. chitosan; celluloses, acrylate polymers, and the like. The selection of coating may be determined by the desired rate of degradation after administration, by targeting to a desired tissue, by protection from oxidation, and the like.

In some specific embodiments, the nanoparticle comprises a coating of polyethylene glycol, which may be conjugated to a polymer used to form the nanoparticle, or may be conjugated to the nanoparticle after it is formed. In some embodiments the coating is polyethylene glycol (PEG) at a molecular weight of from about 1000, from about 2000, from about 5000, up to about 20,000, up to about 15,000, up to about 10,000.

In some embodiments, the payload, for example an effective dose of a cytokine, a TLR2 agonist and a NOD2 agonist, is encapsulated in nanoparticles using a double emulsion water in water solvent evaporation procedure, where the polymer is PLGA conjugated to PEG, and PLA-PEG comprising a maleimide linker group. The active agents may be provided in a weight:weight:weight ratio (IL-2:TLR2 agonist:NOD2 agonist) of about 1:2:2; 1:1:1; 1:2:1; 1:1:2; 1:3:3; 1:2:3; 1:3:2; 1:1:3; 1:3:1; etc., where the ratio of total weight active agents to weight of PLGA is around about 1:50; 1:25, 1:10; 1:5, etc. A therapeutic antibody, for example an agonist of a T cell costimulatory protein such as an anti-CD28 antibody, is conjugated to the resulting nanoparticle through the maleimide linker.

The nanoparticles of the invention may be incorporated in a pharmaceutical formulation. Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

Methods of Use

For the treatment of cancer, the nanoparticles can be administered as a single agent; in combination with a tumor-associated antigen, in combination with additional immunoregulatory agents such an antibody that binds to an inhibits an immune checkpoint protein, etc. Administration can be repeated as required, e.g. dosing 1, 2, 3, 4, 5, 6, 7, 8, 9, 10, 11, 12, etc. times, where the interval between doses can be, for example, 1 day, two days, 3 days, 4 days, 5 days, 6 days, 1 week, 2 weeks, 1 month, etc., and ranges therein, until such time as the desired effect is obtained. The initial dose(s) can be a priming dose, e.g. a lower dose than the therapeutic dose, or can be a higher dose than the therapeutic dose.

Examples of symptoms, illnesses, and/or diseases that can be treated with nanoparticles of the invention include, but are not limited to cancer, which may be any form of cancer, including but not limited to carcinoma, sarcoma, lymphoma, myeloma, teratoma, and cancer of the central nervous system: and an immunological disease or disorder (e.g., an inflammatory disease)(e.g., multiple sclerosis, arthritis, and the like, e.g., for immunosuppressive therapy).

As used herein "cancer" includes any form of cancer, including but not limited to solid tumor cancers (e.g., lung, prostate, breast, bladder, colon, ovarian, pancreas, kidney, liver, glioblastoma, medulloblastoma, leiomyosarcoma, head & neck squamous cell carcinomas, melanomas, neuroendocrine; etc.) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors.

Carcinomas are malignancies that originate in the epithelial tissues. Epithelial cells cover the external surface of the body, line the internal cavities, and form the lining of glandular tissues. Histological types of carcinomas include adenocarcinoma, squamous cell carcinoma, adenosquamous carcinoma, large cell carcinoma, small cell carcinoma, and anaplastic carcinoma. Carcinomas may be found in skin, lungs, pancreas, mouth, throat, esophagus, stomach, colon, breast, prostate, bladder, kidney, anus, ovary, brain and liver, etc.

Examples of carcinomas include, but are not limited to: adenocarcinoma (cancer that begins in glandular (secretory) cells), e.g., cancers of the breast, pancreas, lung, prostate, and colon can be adenocarcinomas; adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like.

Soft tissue tumors are a highly diverse group of rare tumors that are derived from connective tissue. Examples of soft tissue tumors include, but are not limited to: alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; and pleomorphic adenoma of soft tissue; and neoplasias derived from fibroblasts, myofibroblasts, histiocytes, vascular cells/endothelial cells and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to: askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopencytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; undifferentiated pleomorphic sarcoma, and the like).

A teratomas is a type of germ cell tumor that may contain several different types of tissue (e.g., can include tissues derived from any and/or all of the three germ layers: endoderm, mesoderm, and ectoderm), including for example, hair, muscle, and bone. Teratomas occur most often in the ovaries in women, the testicles in men, and the tailbone in children.

Melanoma is a form of cancer that begins in melanocytes (cells that make the pigment melanin). It may begin in a mole (skin melanoma), but can also begin in other pigmented tissues, such as in the eye or in the intestines.

Leukemias are cancers that start in blood-forming tissue, such as the bone marrow, and causes large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is effected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to: Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One kind is Hodgkin lymphoma (HL), which is marked by the presence of a type of cell called the Reed-Sternberg cell. There are currently 6 recognized types of HL. Examples of Hodgkin lymphomas include: nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to: AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to: gliomas (e.g., glioblastomas, astrocytomas, oligodendrogliomas, ependymomas, and the like), meningiomas, pituitary adenomas, vestibular schwannomas, primitive neuroectodermal tumors (medulloblastomas), etc. and may include any of the following diffuse astrocytoma, gemistocytic astrocytoma, oligoastrocytoma, oligodendroglioma, anaplastic astrocytoma, anaplastic oligoastrocytoma, anaplastic oligodendroglioma, glioblastoma, giant cell glioblastoma, gliosarcoma, diffuse midline glioma, pilocytic astrocytoma, subependymal giant cell astrocytoma, pilomyxoid astrocytoma, pleomorphic xanthoastrocytoma, anaplastic pleomorphic xanthoastrocytoma, subependymoma, myxopapillary ependymoma, ependymoma, papillary ependymoma, clear cell ependymoma, tanycytic ependymoma, anaplastic ependymoma, angiocentric glioma, chordoid glioma of the third ventricle, astroblastoma, choroid plexus papilloma, atypical choroid plexus papilloma, choroid plexus carcinoma, desmoplastic infantile astrocytoma and ganglioglioma, dysembryoplastic neuroepithelial tumour (DNET), dysplastic gangliocytoma of the cerebellum, gangliocytoma, ganglioglioma, papillary glioneuronal tumour, paraganglioma of the filum terminale, rosette-forming glioneuronal tumour of the fourth ventricle, central neurocytoma, extraventricular neurocytoma, cerebellar liponeurocytoma, anaplastic ganglioglioma, diffuse leptomeningeal glioneuronal tumour, pineocytoma, pineal parenchymal tumour of intermediate differentiation, papillary tumour of the pineal region, pineoblastoma, medulloblastoma, CNS neuroblastoma, CNS ganglioneuroblastoma, embryonal tumours with multilayered rosettes, medulloepithelioma, atypical teratoid/rhabdoid tumour, CNS embryonal tumour with rhabdoid features, CNS embryonal tumour, schwannoma, cellular schwannoma, plexiform schwannoma, melanotic schwannoma, neurofibroma, atypical neurofibroma, plexiform neurofibroma, perineunoma, malignant peripheral nerve sheath tumour (MPNST), meningioma, meningothelial meningioma, fibrous meningioma, microcystic meningioma, psammomatous meningioma, angiomatous meningioma, secretory meningioma, metaplastic meningioma, lymphoplasmacyte-rich meningioma, atypical meningioma, clear cell meningioma, chordoid meningioma, anaplastic meningioma, papillary meningioma, rhabdoid meningioma, solitary fibrous tumour of the dura/haemangiopericytoma, angiolipoma, chondroma, desmoid-type fibromatosis, haemangioblastoma, haemangioma, hibemoma, leiomyoma, lipoma, myofibroblastoma, osteochondroma, osteoma, rhabdomyoma, epithelioid haemangioendothelioma, angiosarcoma, chondrosarcoma, Ewing sarcoma, fibrosarcoma, Kaposi sarcoma, leiomyosarcoma, liposarcoma, osteosarcoma, rhabdomyosarcoma, undifferentiated pleomorphic sarcoma/malignant fibrous histiocytoma, meningeal melanocytosis, meningeal melanocytoma, meningeal melanomatosis, meningeal melanoma, Erdheim-Chester disease, histiocytic sarcoma, juvenile xanthogranuloma, Langerhans cell histiocytosis, Rosai-Dorfman disease, choriocarcinoma, embryonal carcinoma, germinoma, mixed germ cell tumours, teratoma, yolk sac tumour, craniopharyngioma, adamantinomatous, papillary, granular cell tumour, pituicytoma, and spindle cell oncocytoma.

The nanoparticles can be co-administered with one or more immunoregulatory agents, e.g. antibodies that inhibit immune checkpoint proteins; or antibodies that agonize an immune costimulatory molecule; etc. The immunoregulatory agent may be administered in a combined formulation with the polymeric nanoparticle, or may be administered in a separate formulation. If administered in separate formulations, the administration may be at the same time, or may be administered at different times but sufficiently close so as to have a combined effect, e.g. within a day, two days, 3 days, a week, and the like. Effective doses of combined agents can vary depending upon many different factors, including means of administration, target site, physiological state of the patient, whether the patient is human or an animal, other medications administered, and whether treatment is prophylactic or therapeutic.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

While the human immune system is often able to protect the body from infectious pathogens, it has multiple mechanisms to inhibit mounting an immune system against what it perceives as "self" and thus often fails to eliminate cancer cells since they seem to have the characteristics of "self". Recently, our lab found that self-peptide MHC-specific CD8+ T cells in the blood of healthy humans were present in frequencies similar to those specific for non-self antigens, but these cells are resistant to activation and/or expansion, except with a very strong stimulus (anti-CD3 plus anti-CD28 antibodies).

We hypothesized that tumor infiltrating T cells are often in an anergized or exhausted state but that they could be activated with the appropriate innate immunity signals in addition to antigen-MHC exposure. To test this idea, we have screened a series of combinations of immunological stimulants. In order to activate these cells, however, a large dose of stimulating agents needs to be injected into the body. Those drugs often have life-threatening side effects. For example, one class of these drugs that has been tested in clinical trials is interleukins-naturally occurring chemicals that help promote T cell growth but have severe side effects, including heart and lung failure, when given in large doses.

Figure 1:
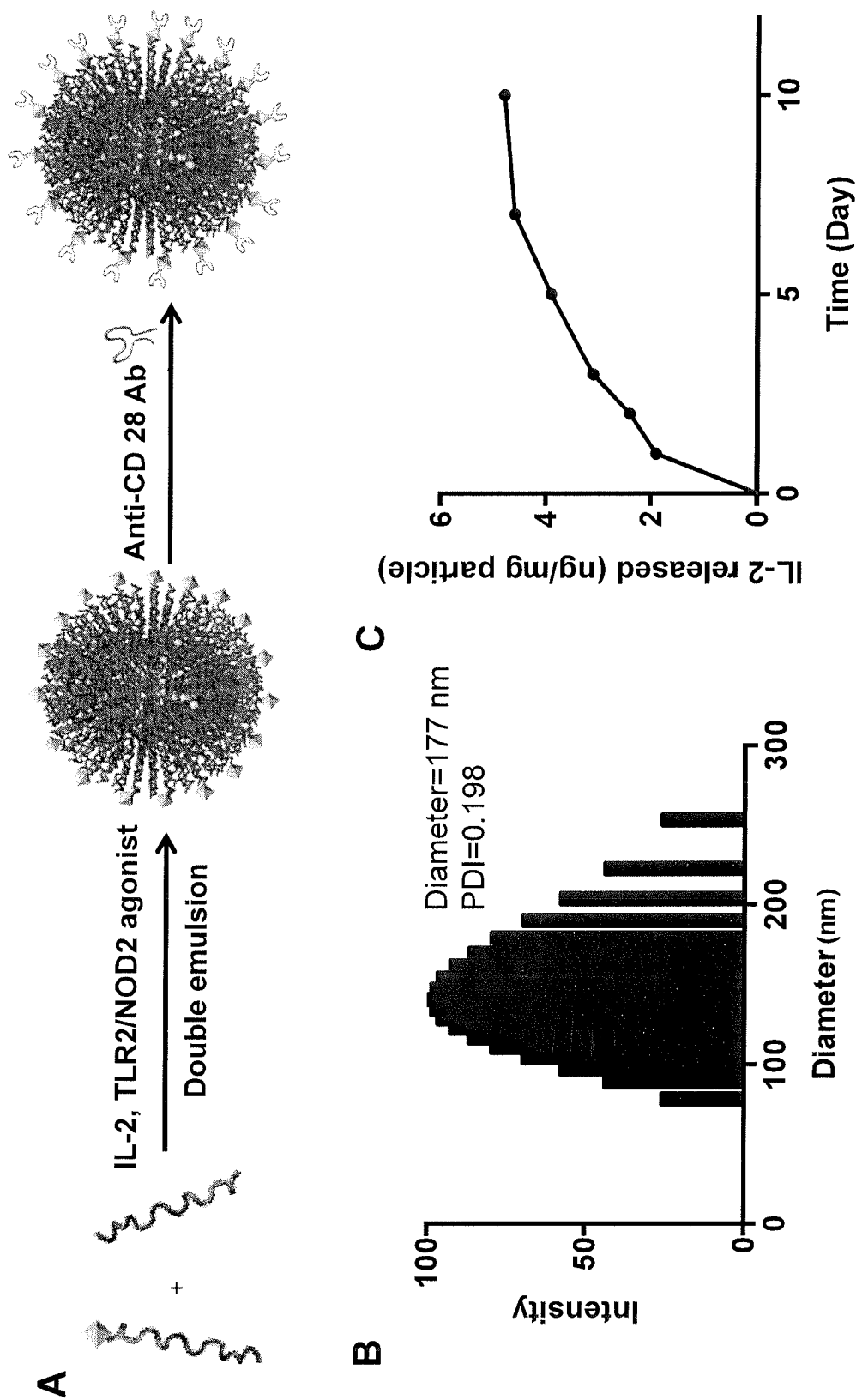
FIG. 1. (A) Schematic illustration of the formulation of stimulatory PLGA nanoparticles (PLGA NPs): IL-2, TLR2 agonist and NOD2 agonist are encapsulated into the NPs through double emulsion and anti-CD28 Ab are conjugated on the surfaces of NPs through maleimide reaction. (B) Dynamic light scattering measurement of particle size and distribution (C) Release kinetics of IL-2 from particles.

To address this issue, we have developed a poly(lactide-co-glycolide) nanoparticle (PLGA NP) based immunostimulatory platform which is functionalized with conjugated monoclonal anti-CD28 antibody (Ab), and can sustainably release encapsulated interleukin-2 (IL-2), toll-like receptor-2 (TLR2) agonist and cytosolic nucleotide-binding oligomerization domain receptor 2 (NOD2) agonist, providing sustained immune stimulation in the tumor microenvironment to continuously activate non-responsive self-specific CD8+ T cells. A schematic of the polymeric nanoparticle formulation is provided in FIG. 1. Compared to systemic administration of stimuli, the favorable release kinetics provided by stimulatory PLGA NPs also allows for minimal systemic toxicity often associated with systemic immunostimulation.

The results demonstrated that the mice with melanoma treated with the developed NPs have elicited potent immune response with markedly increased self-specific effector memory CD8+ T cells in the tumor tissue, resulting in significantly delayed tumor growth. In addition, the developed NPs can also be combined with current immunotherapeutic treatments such as checkpoint blocking antibodies to enhance the effect of these immunotherapeutic treatments, significantly prolonged the overall mice survival.

The nanoparticles described herein deliver immunostimulators including interleukin 2 (IL-2), toll like receptor 2 (TLR2) agonist and nucleotide-binding oligomerization domains 2 (NOD2) agonist in a controlled manner, enabling the continuous activation of non-functional T cells, for example anergic or exhausted self-specific CD8+ T cells in the tumor microenvironment to enhance antitumor immune response while minimizing systemic side effects. Stimulatory PLGA NPs deliver innate signals and induce activation and maturation of tumor dendritic cells, leading them to efficiently present antigen to T lymphocytes, thus initiating an adaptive immune response.

In some experiments, specifically those depicted in FIGS. 3, 4, 5, 6, 9, 10, 11, 12, 13 and 14, the experimental conditions included co-administration of TRP2 180-188 peptide (SEQ ID NO:1) SVYDFFVWL at the dose and timing indicated. Unless indicated, exogenous antigen was not administered.

For all experiments providing a comparison with soluble agents, the doses of the agents encapsulated into the stimulatory NPs are the equivalent to those in the soluble mixture. The dose information provided applies to both soluble and encapsulated agents.

Example 1

Anti-CD28 Ab functionalized, IL-2, TLR2 agonist and NOD2 agonist encapsulating poly(lactide-co-glycolide) nanoparticles (stimulatory PLGA NPs) were prepared using the water-in-oil-in-water (W/O/W) solvent evaporation procedure (also known as the double emulsion method). In brief, 100 μL aqueous solution containing the mixture of 20 μg IL-2, 40 μg TLR2 agonist (Pam3csk4) and 40 μg NOD2 agonist (L18-MDP) were emulsified in a mix of 1.5 ml chloroform solution of PEG-PLGA (20 mg/mL), and 0.5 mL chloroform solution of PLA-PEG-maleimide (10 mg/mL), using a probe sonicator for 1 min. The emulsion was then poured into 20 ml of PVA (1%) aqueous solution, and the mixture was homogenized for 1 min using the sonicator. The resulting emulsion was poured into 80 ml of aqueous PVA (0.3%) with gentle stirring, after which the organic solvent was evaporated by stirring at room temperature for 3 hr in the hood.

The NPs were isolated by centrifugation at 15,000 rpm for 10 min, washed with distilled (DI) water (4 mL×3 times), and dispersed in DI water (2 ml). To modify the NP surface with anti-CD28 Ab, 100 μg Ab (4 mg/ml) were treated with 1.8 mM DTT in the presence of 10 mM EDTA at 25° C. for 30 min to expose hinge region free thiols. DTT was subsequently removed by using Zeba desalting columns before mixing with maleimide-bearing stimulatory PLGA NPs (15 mg/mL) in water at 4° C. for reacting overnight. The stimulatory PLGA NP was then centrifuged at 15,000 rpm for 10 min, washed with DI water (2 mL×3 times), and dispersed in DI water for use. Significant loss of nanoparticles was not observed when re-dispersed in water.

The TLR2 agonist: Pam3csk4 (invivogen); the NOD2 agonist: L18-MDP (invivogen).

Results

Figure 2:
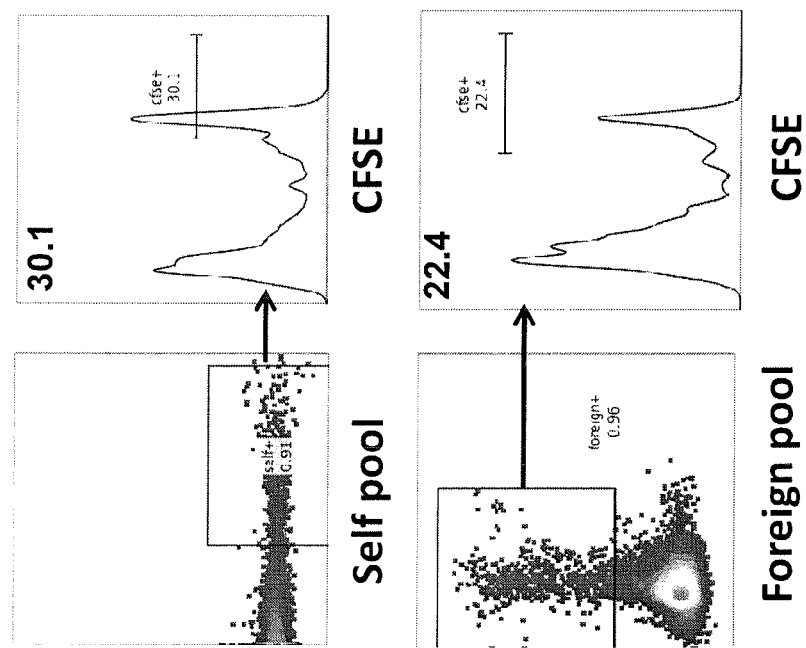
FIG. 2. An equal number of self-versus foreign-specific $CD8^+$ T cells from human healthy blood donors were sorted with two pools of HLA-A*0201 tetramers (one pool loaded with six self peptides including gp100, fibrinogen, PPI, FBA, KER, and GAD, the other with four foreign peptides including human immunodeficiency virus (HIV), Avian influenza virus (H5N1), hepatitis C virus (HCV) and Cytomegalovirus (CMV) to which the blood donors should be naive) into separate wells containing autologous PBMCs. The sorted cells were stimulated with two pools of peptides (the same peptides with which they are tetramer selected) as well as stimulatory PLGA NPs. The extent of cell proliferation was determined by enumerating the number of $tetramer^+CD8^+$ T cells and analyzing CFSE (Carboxyfluorescein succinimidyl ester) dilution by flow cytometry.
Figure 3:
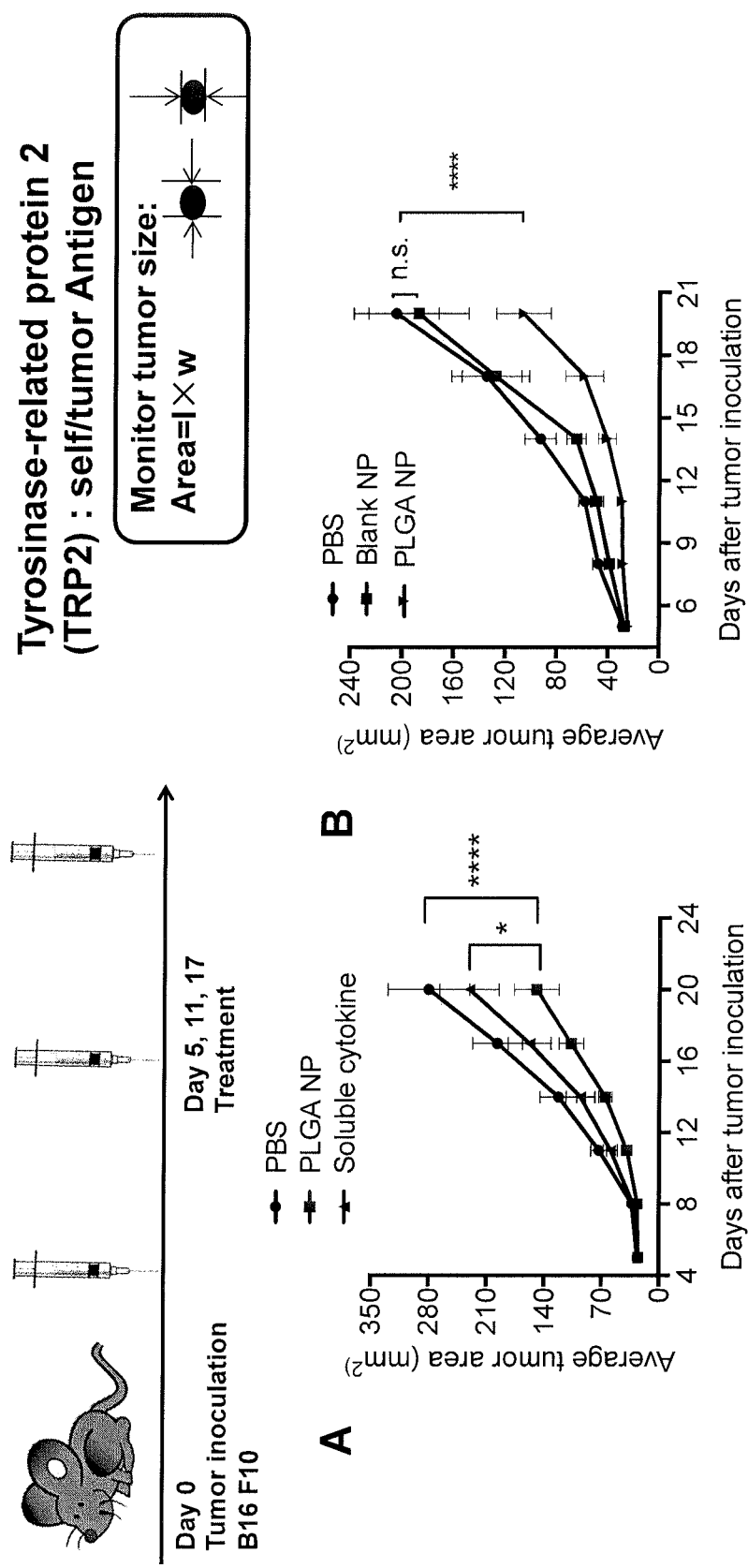
FIG. 3. Antitumor efficacy of stimulatory PLGA NP in murine B16F10 melanoma. (A) The average tumor growth curve of B16F10 melanoma treated with PBS, stimulatory PLGA NP plus TRP2 antigen or a mixture of soluble IL-2, TLR2 agonist, NOD2 agonist and anti-CD28 Ab plus TRP2 antigen (soluble cytokine). Tumor inoculation was at Day 0, and three treatments were performed at Day 5 (Equivalent dose: 40 ng of IL-2, 2.5 μg of TLR2 agonist, 2.5 μg of NOD2 agonist, 10 μg of anti-CD28 Ab and 10 μg of TRP2 peptide for priming), Day 11 (Equivalent dose: 80 ng of IL-2, 5 μg of TLR2 agonist, 5 μg of NOD2 agonist, 20 μg of anti-CD28 Ab and 20 μg of TRP2 peptide for boosting) and Day 17 (Equivalent dose: 80 ng of IL-2, 5 μg of TLR2 agonist, 5 μg of NOD2 agonist, 20 μg of anti-CD28 Ab and 20 μg of TRP2 peptide for boosting). (n=10) (B) The average tumor growth curve of B16F10 melanoma. Mice were treated with PBS, stimulatory PLGA NP plus TRP2 antigen and the blank PLGA NPs (no immunostimulatory compounds or cytokines in it) plus TRP2 antigen (n=7). **, $p<0.0001$; , $p<0.01$; *, $p<0.05$ by two-way ANOVA.
Figure 4:
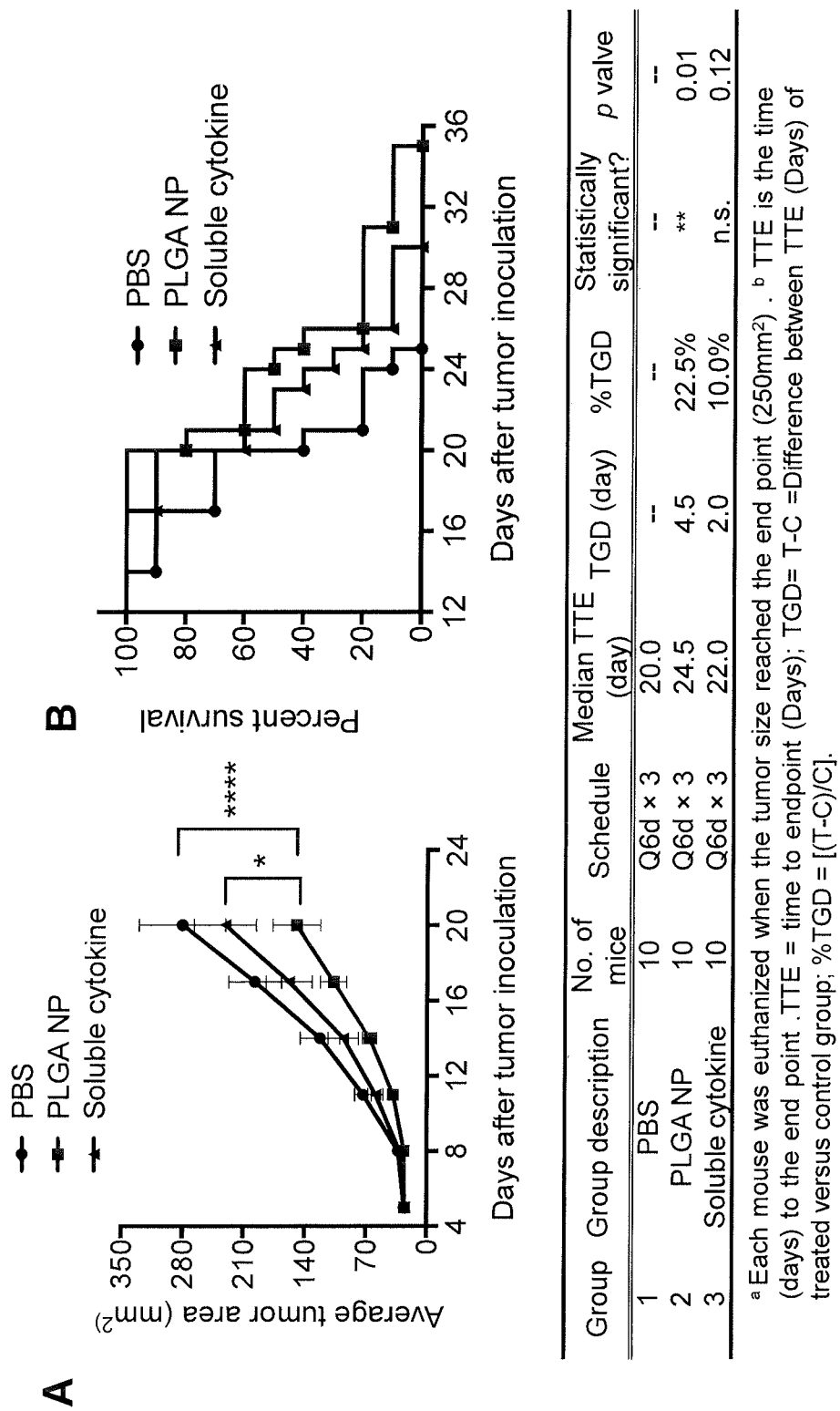
FIG. 4. Antitumor efficacy of stimulatory PLGA NP in murine B16F10 melanoma. (A) The average tumor growth curve of B16F10 melanoma treated with PBS, stimulatory PLGA NP plus TRP2 antigen and mixture of soluble IL-2, TLR2 agonist, NOD2 agonist and anti-CD28 Ab plus TRP2 antigen (soluble cytokine). Tumor inoculation was at Day 0, and three treatments were performed at Day 5 (Equivalent dose: 40 ng of IL-2, 2.5 μg of TLR2 agonist, 2.5 μg of NOD2 agonist, 10 μg of anti-CD28 Ab and 10 μg of TRP2 peptide for priming), Day 11 (Equivalent dose: 80 ng of IL-2, 5 μg of TLR2 agonist, 5 μg of NOD2 agonist, 20 μg of anti-CD28 Ab and 20 μg of TRP2 peptide for boosting) and Day 17 (Equivalent dose: 80 ng of IL-2, 5 μg of TLR2 agonist, 5 μg of NOD2 agonist, 20 μg of anti-CD28 Ab and 20 μg of TRP2 peptide for boosting). (B). The percentage survival of mice after three treatments was monitored over time. **, $p<0.0001$; , $p<0.01$; *, $p<0.05$ by two-way ANOVA.

The capacity of stimulatory PLGA NP to stimulate self-specific CD8+ T cells in human was shown in FIG. 2. Self-specific CD8+ T cells were sorted using pooled HLA-A2 tetramers with self-specific peptides including gp100, fibrinogen, PPI, FBA, KER, and GAD from the peripheral blood of healthy human blood donors and cultured under different conditions in the presence of the pool of peptides used for tetramer staining. The foreign-specific CD8+ T cells were also sorted and cultured as a control. The extent of cell proliferation was determined by analyzing CFSE dilution by flow cytometry.

Shown in FIGS. 3A-3B is the antitumor efficacy of stimulatory PLGA NP in murine B16F10 melanoma. As shown in the tumor growth curve, the nanoparticles encapsulating a payload reduced tumor growth relative to a blank nanoparticle or to the cytokine payload administered in soluble form. Similar results are shown in FIG. 4A. FIG. 4B illustrates the survival curve of mice treated with the nanoparticles or with the cytokine payload in soluble form, where it is shown that there is a statistically significant difference between the treatment with free and encapsulated cytokine payload.

Figure 5:
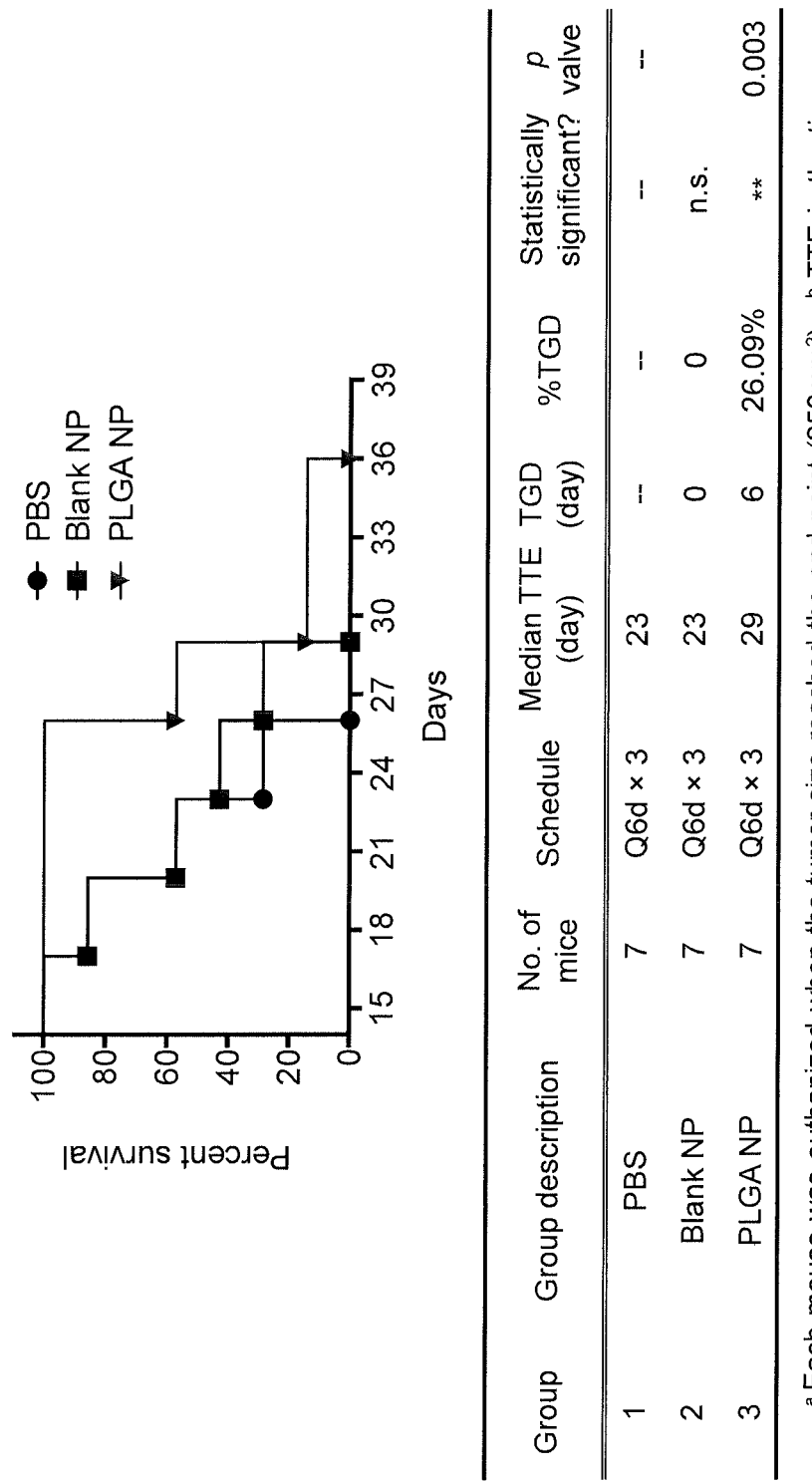
FIG. 5. Antitumor efficacy of stimulatory PLGA NP in murine B16F10 melanoma. Tumor inoculation was at Day 0, and three treatments (PBS, stimulatory PLGA NP plus TRP2 antigen and the blank PLGA NPs (no immunostimulatory compounds or cytokines in it) plus TRP2 antigen) were performed at Day 5 (Equivalent dose: 40 ng of IL-2, 2.5 μg of TLR2 agonist, 2.5 μg of NOD2 agonist, 10 μg of anti-CD28 Ab and 10 μg of TRP2 peptide for priming), Day 11 (Equivalent dose: 80 ng of IL-2, 5 μg of TLR2 agonist, 5 μg of NOD2 agonist, 20 μg of anti-CD28 Ab and 20 μg of TRP2 peptide for boosting) and Day 17 (Equivalent dose: 80 ng of IL-2, 5 μg of TLR2 agonist, 5 μg of NOD2 agonist, 20 μg of anti-CD28 Ab and 20 μg of TRP2 peptide for boosting). The percentage survival of mice after three treatments was monitored over time.
Figure 6:
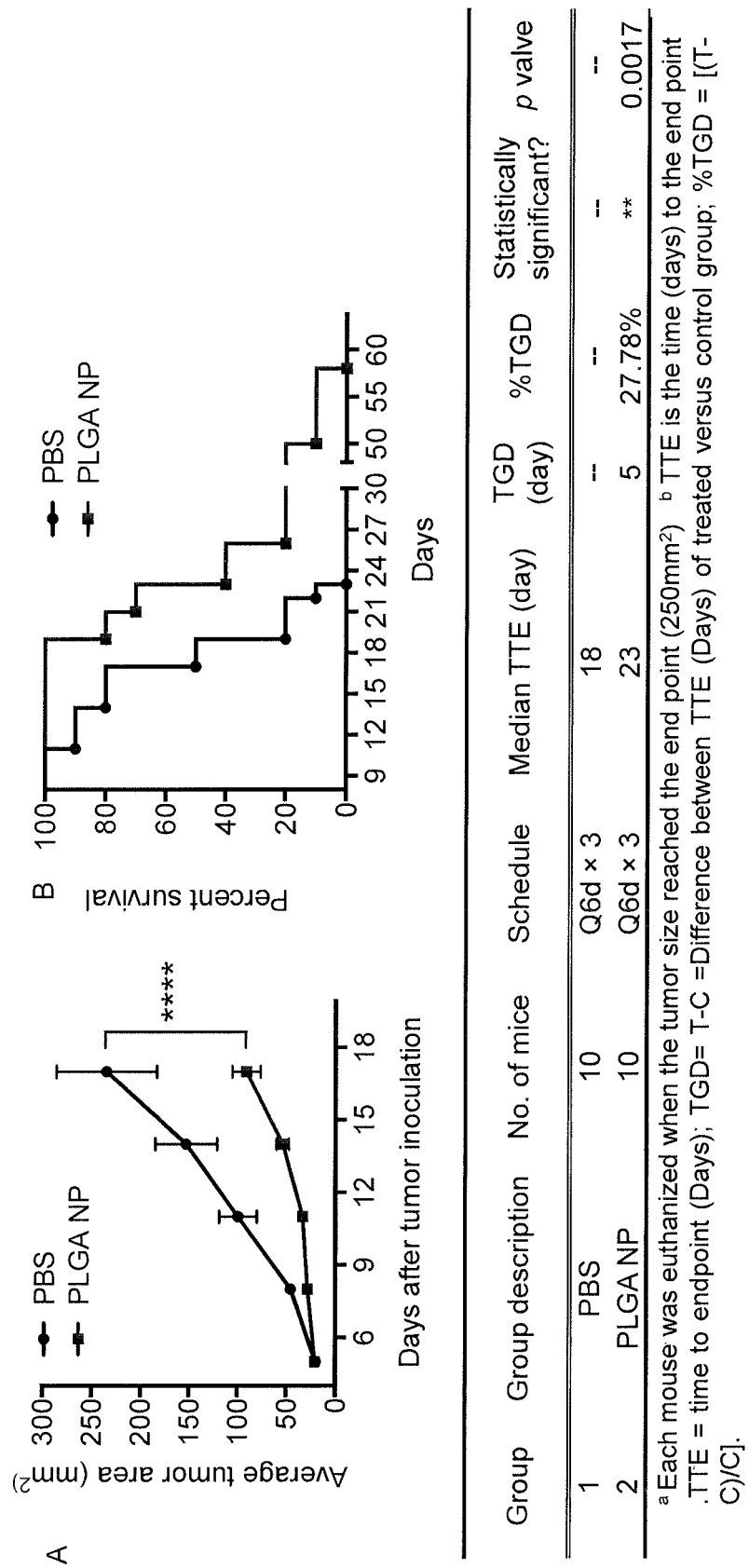
FIG. 6. Antitumor efficacy of stimulatory PLGA NP in murine B16F10 melanoma. (A) The average tumor growth curve of B16F10 melanoma treated with PBS, stimulatory PLGA NP plus TRP2 antigen. Tumor inoculation was at Day 0, and three treatments were performed at Day 5 (Equivalent dose: 40 ng of IL-2, 2.5 μg of TLR2 agonist, 2.5 μg of NOD2 agonist, 10 μg of anti-CD28 Ab and 10 μg of TRP2 peptide for priming), Day 11 (Equivalent dose: 80 ng of IL-2, 5 μg of TLR2 agonist, 5 μg of NOD2 agonist, 20 μg of anti-CD28 Ab and 20 μg of TRP2 peptide for boosting) and Day 17 (Equivalent dose: 80 ng of IL-2, 5 μg of TLR2 agonist, 5 μg of NOD2 agonist, 20 μg of anti-CD28 Ab and 20 μg of TRP2 peptide for boosting). (B). The percentage survival of mice after three treatments was monitored over time. **, $p<0.0001$; , $p<0.01$; *, $p<0.05$ by two-way ANOVA.

Antitumor efficacy of stimulatory PLGA NP in murine B16F10 melanoma is shown in FIG. 5, comparing three treatments (PBS, stimulatory PLGA NP plus TRP2 antigen and blank PLGA NPs (lacking cytokines) plus TRP2 antigen). The survival curve shows a statistically significant improvement in animals treated with the polymeric nanoparticles, versus tumor antigen and blank nanoparticles. FIG. 6 shows the average tumor growth curve and survival curve of animals inoculated with B16F10 melanoma treated with PBS, or with stimulatory PLGA NP and TRP2 antigen.

Figure 7:
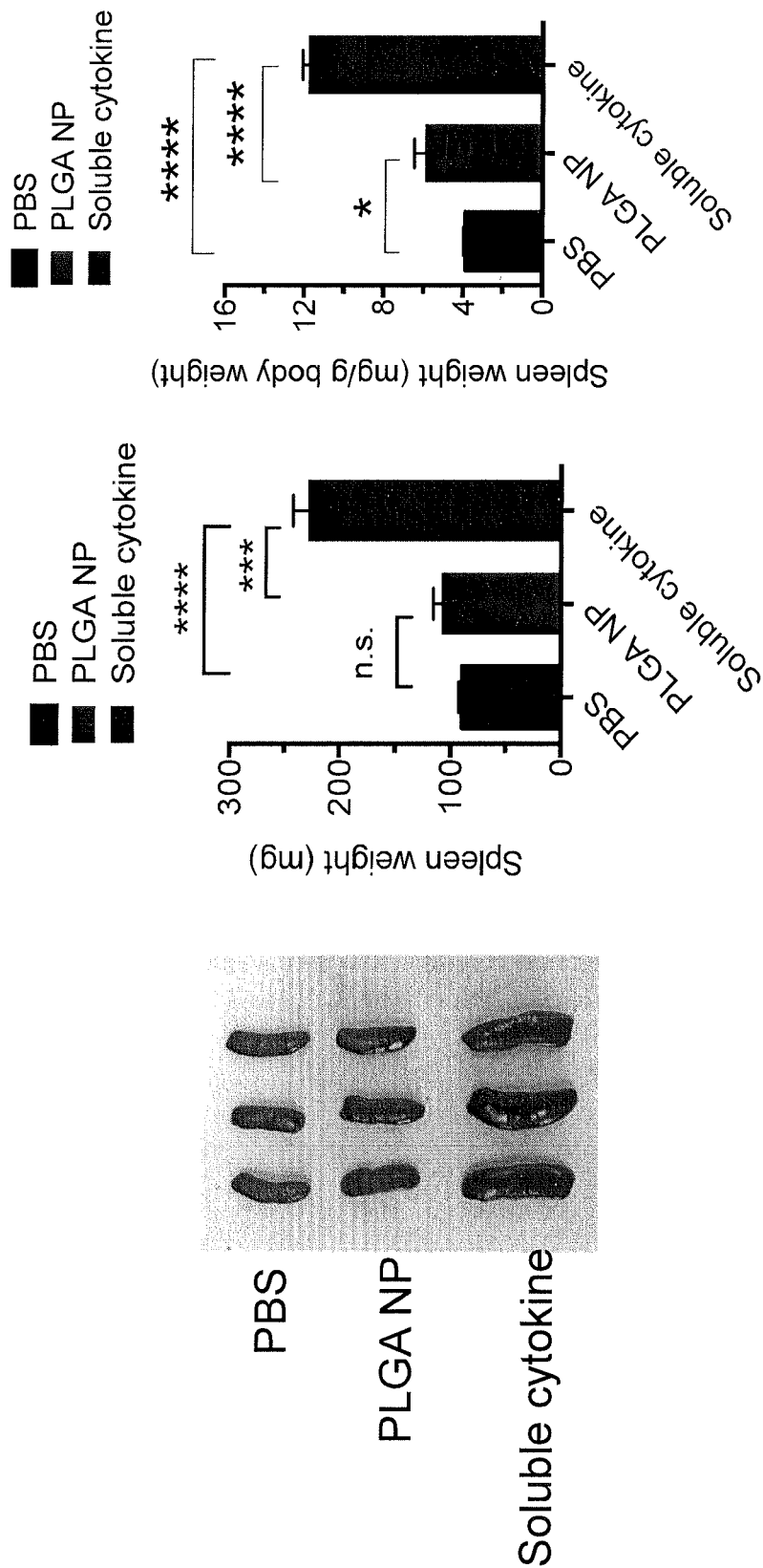
FIG. 7. Splenomegaly assessed on Day 7 after three injections (Day 1, Day 3 and Day 5) of PBS, PLGA NP and soluble cytokines. bw, body weight. *$p<0.001$, $p<0.01$, *$p<0.05$ by one-way ANOVA with Bonferroni post-test (n=3).

Splenomegaly was assessed on Day 7 after three injections (Day 1, Day 3 and Day 5) of PBS, stimulatory PLGA NP and soluble cytokines, as shown in FIG. 7. The spleen weight was significantly increased with soluble cytokine payload, versus the encapsulated cytokines in the nanoparticle formulation.

Figure 8:
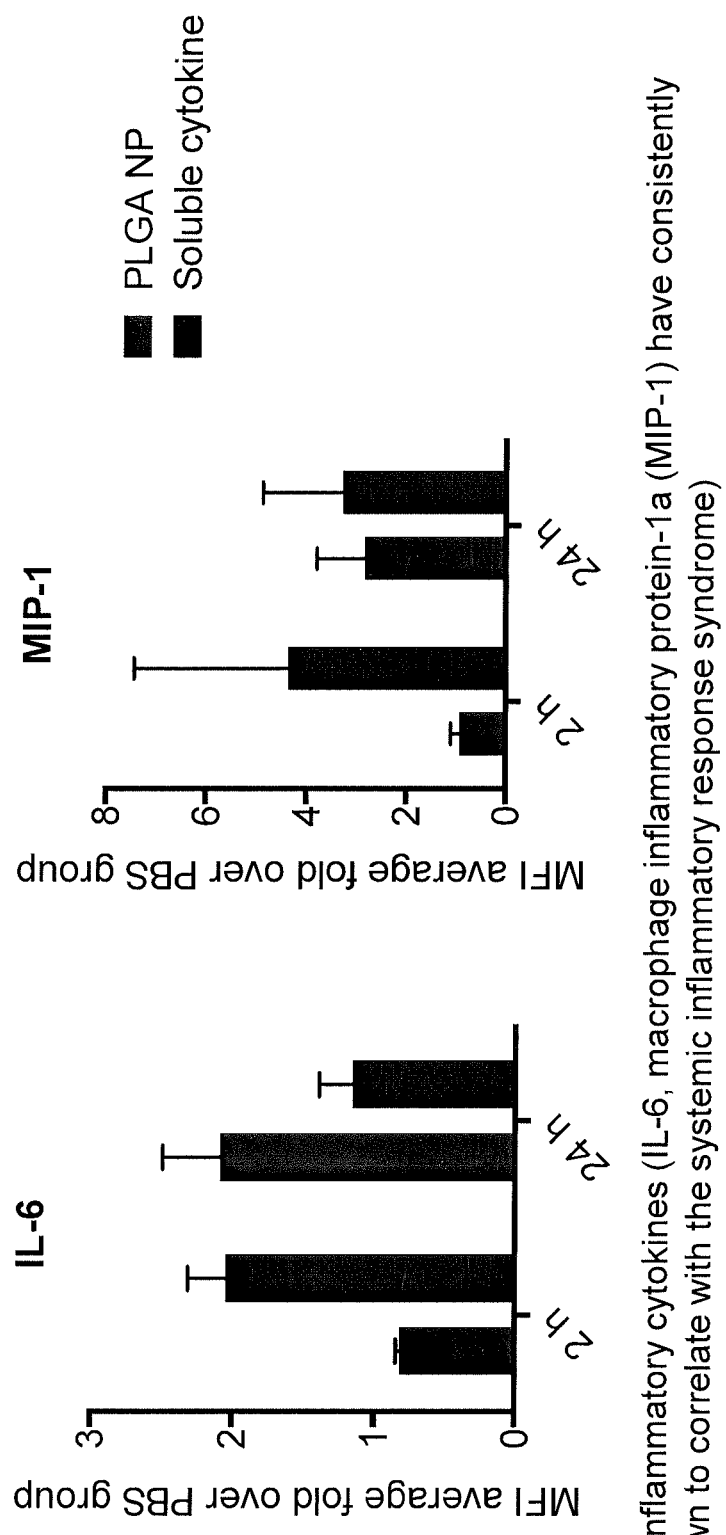
FIG. 8. Serum cytokines (IL-6) and MIP-1 assessed on 2 h and 24 h after the injection of PLGA NP and soluble cytokines. (n=3).
Figure 9:
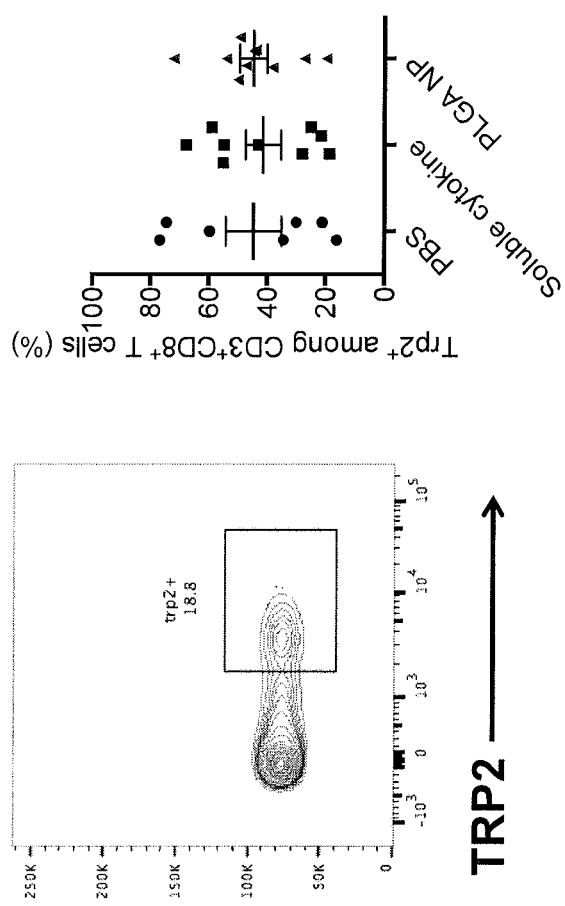
FIG. 9. Tetramer staining of self-specific ($TRP2^+CD8^+$ T cells in murine melanoma after treatment by PBS, stimulatory PLGA NP and soluble cytokine. Tumor inoculation was at Day 0, and two treatments were performed at Day 5 (Equivalent dose: 40 ng of IL-2, 2.5 μg of TLR2 agonist, 2.5 μg of NOD2 agonist, 10 μg of anti-CD28 Ab and 10 μg of TRP2 peptide for priming) and Day 11 (Equivalent dose: 80 ng of IL-2, 5 μg of TLR2 agonist, 5 μg of NOD2 agonist, 20

Serum cytokines (IL-6) and MIP-1 from a blood sample of a mouse were assessed on 2 h and 24 h after the injection of stimulatory PLGA NP and soluble cytokines. Shown in FIG. 8, it can be seen that administration of soluble cytokines resulted in a short term increase of pro-inflammatory cytokines, while the nanoparticles increased cytokine production over a 24 hour time period. Shown in FIG. 9, there is no difference between treatments in terms of the frequency of TRP2$^+$ CD8$^+$ T cells in the tumor. The effect of stimulatory PLGA NPs reversed the function of self-specific CD8$^+$ T cells, but had little effect on their frequency.

Stimulatory PLGA NPs elicit potent T cell response in tumor by activating the self-specific (TRP2$^+$CD8$^+$ T cells in tumor. As shown in FIG. 10, the activation marker (CD25, CD44 and CD69) were significantly unregulated in animals after treatment with stimulatory PLGA NPs. Tumor inoculation was at Day 0, and two treatments were performed at Day 5 (40 ng of IL-2, 2.5 µg of TLR2 agonist, 2.5 µg of NOD2 agonist, 10 µg of anti-CD28 Ab and 10 µg of TRP2 peptide for priming) and Day 11 (80 ng of IL-2, 5 µg of TLR2 agonist, 5 µg of NOD2 agonist, 20 µg of anti-CD28 Ab and 20 µg of TRP2 peptide for boosting). Tumor infiltrating T cells were isolated for analysis on Day 17. The tumor-infiltrating cells also had increased expansion of TNFα and IFN-γ producing CD8$^+$ population in tumor after treatment with stimulatory PLGA NPs, as shown in FIG. 11. Treatment with the nanoparticles drives a T cell response that is strongly biased toward effector memory (CD44$^{hi}$CD62L$^{lo}$) populations in the tumor, and is increased relative to administration of soluble cytokines. As shown in FIG. 13, expression of a number of pro-inflammatory cytokines is increased in the microenvironment of an established tumor. GCSF (Granulocyte colony-stimulating factor): stimulates the survival, proliferation, differentiation and function of neutrophil precursors and neutrophils. LIX: LPS-induced CXC chemokine (closely related to human CXCL5) is pro-inflammatory chemokine and is chemotactic for neutrophils. IL-1beta is produced by activated macrophage and dendritic cells, which is presumably in response to TLR and NOD signaling as a result of activation of NF-κB pathway: IL-1beta in turn will influence the subsequent adaptive immune response.

Administration of the nanoparticles also enhances antigen presentation and activation of dendritic cells, evidenced by expression of MHC Class II antigens, CD80, and CD86 in the tumor. Tumor inoculation was at Day 0, and two treatments were performed at Day 5 (40 ng of IL-2, 2.5 µg of TLR2 agonist, 2.5 µg of NOD2 agonist, 10 µg of anti-CD28 Ab and 10 µg of TRP2 peptide for priming) and Day 11 (80 ng of IL-2, 5 µg of TLR2 agonist, 5 µg of NOD2 agonist, 20 µg of anti-CD28 Ab and 20 µg of TRP2 peptide for boosting). Tumor infiltrating T cells were isolated for analysis on Day 17 (n=3). The results are shown in FIG. 14.

Results showed the stimulatory PLGA NPs were capable of facilitating the maturation of DCs, promoting their efficiency as antigen presenting cell, as evidenced by the up-regulation of the expression MHC class II (FIG. 14). Notably, there is enhancement of cross-presentation by DC and proliferation of OT1-specific CD8$^+$ T cells after the treatment of stimulatory PLGA NPs containing TLR2 and NOD2 agonists (FIG. 15 and FIG. 16). TLR2 receptors are expressed on the cell surface and so widely exposed to ligands, but NOD2 receptors are within cytoplasm and are exposed to few diffusing L18-MDP. The stimulatory PLGA NPs could increase the uptake efficiency of TLR2 and NOD2 agonists by DCs, thus provided stronger adjuvant effect, which is demonstrated by FACs analysis that the profound increase of fluorescence intensity in DCs after co-incubation with NP encapsulated rhodamine-labeled TLR2 and NOD2 agonists compared to those co-incubated with soluble rhodamine-labeled TLR2 and NOD2 agonists (FIG. 17).

As shown in FIG. 18, nanoparticles also enhance the activation of RAW macrophages bearing a NF-κB reporter as compared to soluble TLR2 and NOD2 agonists. TLR2 and NOD2 agonists containing stimulatory PLGA NPs or mixture of TLR2 and NOD2 were incubated for 24 hours with the InvivoGen HEK-BLUE™ murine TLR2 reporter cell line, a secreted embryonic alkaline phosphatase (SEAP) reporter system. SEAP levels were quantified by incubating supernatant with QUANTIBLUE™ substrate for 1 h and reading absorption at 620 nm. The data show that there is increased NF-κB activity in the presence of the nanoparticles compared to the soluble agonists.

Example 2

Materials. mPEG-PLGA(LG 50:50 (w:w), Mw 5000: 10000 Da), PLGA-PEG-Maleimide (Mw 1500-5000 PLGA-PEG) was purchased from Akina, Inc. (West Lafayette, IN, USA). TRP2180-188 (SVYDFFVWL) (HPLC purity>95%) was synthesized by Elim Biopharmaceuticals, Inc. (Hayward, CA, USA). TLR2 agonist (Pam3CSK4) and NOD2 agonist (L18-MDP) were purchased from InvivoGen (San Diego, CA, USA). Ovalbumin protein was purchased from Worthington biochemical Corporation. H2-Kb TRP2 tetramer-PE was purchased from MBL international corporation (Wobum, MA, USA). All other chemical reagents were purchased from Sigma-Aldrich and used as received except where otherwise noted.

Cell culture. B16F10 cells were purchased from American Type Culture Collection (ATCC) and cultured in DMEM medium containing 10% fetal bovine serum (FBS) and 100 units/mL aqueous Penicillin G sodium and 100 µg/mL streptomycin (Pen/Strep) at 37° C. in 5% CO$_2$ humidified air. MC38 cells were purchased from Kerafast, Inc and cultured in DMEM medium containing 10% FBS, 2 mM glutamine, 0.1 mM nonessential amino acids, 1 mM sodium pyruvate, 10 mM Hepes, 50 µg/mL gentamycin sulfate, Pen/Strep. TLR2 reporter cell line RAW-BLUE™ cells were purchased from invivogen (San Diego, CA, USA) and cultured in DMEM medium containing 10% FBS, 100 mg/mL NORMOCIN™, 2 mM glutamine and 200 µg/mL ZEOCIN™.

Animals. 6-8 weeks old female C57BL/6J mice were purchased from the Jackson Laboratory. All the animals were cared in Stanford Animal Facility under federal, state and NIH guidelines. The study protocol was reviewed and approved by the University Administrative Panel on Laboratory Animal Care.

General Procedures of the Preparation of Anti-CD28 Ab Functionalized, IL-2, TLR2 Agonist and NOD2 Agonist Encapsulating Poly(Lactide-Co-Glycolide) Nanoparticles (PLGA NPs).

Drug encapsulation. The stimulatory PLGA NPs were prepared using the water-in-oil-in-water (W/O/W) solvent evaporation procedure (also known as the double emulsion method). In general, 100 µL aqueous solution of the mixture of IL-2 (20 µg), TLR2 agonist (Pam3csk4, 40 µg) and NOD2 agonist (L18-MDP, 40 µg) were emulsified in a mix of chloroform solution of PEG-PLGA (20 mg/mL, 1.5 mL), and PLA-PEG-maleimide (10 mg/mL, 0.5 mL), using a probe sonicator for 1 min. The emulsion was then poured into 20 ml of PVA (1%) aqueous solution, and the mixture was homogenized for 1 min using the sonicator. The resulting emulsion was poured into 80 ml of aqueous PVA (0.3%) with gentle stirring, after which the organic solvent was evaporated by stirring at room temperature for 3 h in the hood. The NPs were collected by centrifugation and washed with distilled (DI) water for later use.

Antibody conjugation. To modify the NP surface with anti-CD28 Ab, 100 µg Ab (4 mg/ml) were treated with 1.8 mM DTT in the presence of 10 mM EDTA at 25° C. for 30 min to expose hinge region free thiols. DTT was subsequently removed by using Zeba desalting columns before mixing with maleimide-bearing stimulatory PLGA NPs (15 mg/mL) in water at 4° C. for reacting overnight. The stimulatory PLGA NP was then collected by centrifugation, washed with DI water for later use.

DLS measurements. The hydrodynamic size was measured with 90Plus Particle Size Analyser by dispersing the NPs in DI water at concentration of 0.5 mg/mL. Measurements were taken at a 90° scattering angle.

Release kinetic study of IL-2 from stimulatory PLGA NPs. The stimulatory PLGA NPs were prepared as above mentioned. The collected NPs were dispersed in serum buffer (FBS:PBS=1:1, v/v, 10 mL) and incubated at 37° C. Two aliquots (500 µL) were taken out at scheduled time points. The NPs were removed by the centrifugation and the IL-2 in supernatant was measured by ELISA assay.

In vitro uptake assay. JAWSII DC cells were cultured in the 6-well plate. Rhodamine-labeled TLR2 agonist and NOD2 agonist or stimulatory PLGA NPs encapsulating rhodamine-labeled TLR2 agonist and NOD2 agonist (agonist equivalent dose 1.25 µg/mL) was incubated with JAWSII DC at 37° C. for 4 h. Uptake were quantified using the mean fluorescence intensity (MFI) of DC cells by FACS.

In vitro TLR reporter assay. Soluble mixture of TLR2 agonist and NOD2 agonist or agonists encapsulated stimulatory PLGA NPs were incubated with RAW-BLUE™ mouse macrophage reporter cell line at 37° C. for 24 h. The supernatant was collected and incubate with QUANTIBLUE™ substrate for 1 h. Secreted embryonic alkaline phosphatase (SEAP) levels were quantified by reading the absorption at 620 nm.

In vitro cross-presentation assay. DCs (BMDCs or JAWSII cells) were plated at 15000 cells per well in a 96-well U-bottom plate and incubated with ovalbumin (OVA) (2 µg/mL) and different stimuli (soluble TLR2 agonist, soluble NOD2 agonist, soluble mixture of TLR2 and NOD2 agonist and agonists encapsulated stimulatory PLGA NPs) overnight. DC medium only used as control. DCs were washed three times with PBS and then incubated with 50000 CFSE-labeled OT1 CD8$^+$ T cells using complete RPMI1640 medium (RPMI1640 containing 10% FBS, pen/strep, sodium pyruvate and beta-mercaptoethanol) for 5 days. Cells were collected and stained with CD3, CD4, CD8 and analyzed by Flowjo. The extent of CFSE-labeled OT1 CD8$^+$ T cells were analyzed by calculating CFSE dilution.

Tetramer staining and phenotype analysis. B16F10 tumors were dissected on day 17 and prepared single cell suspension. The cells were washed and blocked with Fc-blocker (anti-mouse CD16/CD32 monoclonal antibody on ice for 10 min). Then cells were stained with PE-labeled TRP2 tetramer (MBL international corporation) and incubated at room temperature for 1 h. Cells were washed twice and then stained with surface markers (CD45, CD3, TCRb, CD4, CD8, CD44, CD62L, CD69, CD25), and analyzed on BD LSRII flow cytometer.

Intracellular cytokine staining. B16F10 tumors were dissected on day 17 and prepared single cell suspension. The cells were plated in 24-well plates and stimulated with either EBIOSCIENCE™ Cell Stimulation Cocktail for 5 h at 37° C. or TRP2180-188 peptide (SVYDFFVWL) for 16 h at 37° C. After stimulation, the cells were washed, blocked with Fc-blocker (anti-mouse CD16/CD32 monoclonal antibody on ice for 10 min) and stained with stained with CD45, CD3, TCRb, CD4, CD8. Cells were then fixed with Foxp3 Fixation/Permeabilization working solution (ebioscience) according to the manufacturer's instructions, washed and permeabilized for the staining with anti-IFNγ, anti-TNF, anti-IL17A and anti-Foxp3. Cells were then analyzed on a BD LSRII flow cytometer.

Tumor efficacy study. Female C57Bl/6 mice (6-8 weeks) were anaesthetized and inoculated subcutaneously onto the right flank with 1×10$^5$ B16F10 murine melanoma tumor cells or 5×10$^5$ MC38 murine colon cancer cells. On Day 5 (for B16F10) or Day 9 (for MC38), mice with established tumors were randomly divided into groups (n=10 for B16F10 or n=6 for MC38), minimizing weight and tumor size difference among the groups. B16F10 tumor bearing mice treated three times on Day 5, Day 11 and Day 17 through intratumoral injection of PBS (1×, 50 µL) and stimulatory PLGA NPs (160 ng of IL-2, 10 µg of NOD2 agonist, 10 µg of TLR2 agonist and 20 µg of anti-CD28 Ab), respectively. MC38 tumor bearing mice were treated three times on Day 9, Day 14 and Day 19 through intratumoral injection of PBS (1×, 50 µL) and stimulatory PLGA NPs (160 ng of IL-2, 10 µg of NOD2 agonist, 10 µg of TLR2 agonist and 20 µg of anti-CD28 Ab), respectively. The body weight and tumor sizes of animals were monitored every 2 or 3 days. The tumor sizes were monitored by calipers and calculated according to the formula (length)×(width) or (length)×(width)$^2$/2. If body weight loss is beyond 20% of pre-dosing weight, the animals were euthanized. When the tumor load reached 200 mm$^2$ or 900 mm$^3$ (as predetermined endpoint) or the animal had become moribund, the mouse was sacrificed.

Splenomegaly measurements. Female C57B/6 mice (6-8 weeks) were injected subcutaneously with PBS, stimulatory PLGA NPs and free cytokine mixture at Day 1, Day 3 and Day 5. Spleens were collected at Day 7 after three injections. The sample was normalized to individual mouse body weight.

Intratumoral cytokine measurements. Female C57B/6 mice (6-8 weeks) were anaesthetized and inoculated subcutaneously onto the right flank with $1\times10^5$ B16F10 murine melanoma tumor cells. On Day 5, mice with established tumors were treated two times on Day 5 and Day 11 through intratumoral injection of PBS and stimulatory PLGA NPs, respectively. Tumors were harvested at day 17 and cut into small pieces. Then the tumor were digested with 1 mL Collagenese IV (0.5 mg/mL) and DNAese (10 µg/mL) at 37° C. for 1 h. The cells went through the cell strainer (70 µm) and centrifuged at 4000 rpm for 10 min. The supernatant were aliquoted and stored at −80° C. until analysis. Samples were diluted 1:1 with Assay Buffer and assayed using a Luminex bead-based ELISA following manufacturer's instructions.

Results

The cytotoxic $CD8^+$ T cells which can recognize self-antigens are found in a relatively high frequencies in peripheral blood from both health human and melanoma patients, but they are very resistant to stimulation and activation. In mouse, the self-specific $Trp2^+$ $CD8^+$ T cells are enriched in the tumor compared to lymph node and spleen in mice bearing B16F10 melanoma. But they showed distinct phenotype with heterogeneous CD44 expression. These cells gradually lost their function, as evident by reduced IFNγ production during the tumor progression.

We found these self-specific $CD8^+$ T cells could be activated and proliferated with the innate immunity signals through the combination of IL-2, TLR2 agonist, and NOD2 agonist in addition to peptide-MHC exposure, as shown FIG. 2. However, severe dose-limiting inflammatory toxicity is associated with these adjuvants. To address the safety issue, we developed a nanoparticle-based delivery system that enables the sustained release of adjuvants at the tumor site to minimize the systemic toxicities. The results showed that soluble adjuvant mixture that is not encapsulated in PLGA NPs rapidly drains to the systemic circulation, leading to acute systemic inflammatory toxicities charactering by elevated serum inflammatory cytokines 2 h after single subcutaneous injection of them into the mice. Repeated injections of them resulted in significantly enlarged spleen (splenomegaly). In contrast, both single and repeated injections of stimulatory PLGA NPs showed greatly reduced systemic inflammation relative to soluble mixture.

The developed nanoparticles showed efficacy in delaying tumor growth and prolonging the overall survival in both B16F10 melanoma and MC38 colon cancer models. Notably, the establishment of effective immunological memory has been demonstrated by rejection of the second tumor challenge in both tumor models.

No antigens were administered with PLGA NPs during the treatment in both tumor models for the data presented in FIGS. 19-28. This is particular interest from a practical perspective as it offers the flexibility of the treatment across a variety of tumor types. In the absence of administered tumor antigen, administration of nanoparticles suppresses the tumor growth, and prolongs the overall survival in B16F0 melanoma model and in MC38 colon cancer model (see below). Shown in FIG. 19, there is a significant improvement in average tumor size and survival when animals were treated with nanoparticles.

The nanoparticles also establish the protective immune memory in B16F10 tumor model. A mouse that was inoculated with melanoma cells treated with nanoparticles as described for FIG. 19 and survived was then inoculated with the melanoma cells a second time. It can be seen in FIG. 20 that the animal was able to survive a second tumor challenge as well.

Administration of nanoparticles also suppresses the tumor growth, prolongs the overall survival and establishes the protective memory in a colon cancer model. The average tumor growth curve and survival was determined for animal inoculated with MC38 murine colon cancer treated with PBS or stimulatory PLGA NP. Shown in FIG. 21, there is a significant improvement in average tumor size and survival when animals were treated with nanoparticles.

As shown in FIG. 22, administration of the nanoparticles remodels the tumor microenvironment of established B16F10 melanoma tumor by up-regulating a variety of pro-inflammatory cytokines expression, and induces potent endogenous self-specific CD8 T cell response in B16F10 melanoma model (FIG. 23), driving self-specific ($TRP2^+$ T cell response strongly biased toward effector memory ($CD44^{hi}CD62L^{lo}$) populations in tumor, in the absence of administered antigenic peptides.

Administration of nanoparticles also elicits a potent T cell response in a colon cancer tumor model, as shown in FIG. 24. Nanoparticle administration increased the proportion of $CD8^+$ T cells in the tumor infiltrating T cell population, increased the percentage of $CD44^{hi}CD62L^{low}CD8^+$ T cells, and increased the percentage of $CD8^+$ cells staining for the intracellular cytokine IFNγ and TNFα.

An important finding is the effectiveness of combining the nanoparticles with a checkpoint inhibitor. The combination of PLGA NPs and checkpoint blocking antibody anti-PD-L1 demonstrated enhanced the effect of either treatment alone in B16F10 melanoma model. Shown in FIG. 25, the anti-tumor efficacy of anti-PD-L1 against murine B16F10 melanoma was significantly enhanced by also treating the animals with PLGA NP (A and B), and the antitumor efficacy of PLGA NP against murine B16F10 melanoma was significantly enhanced by also treating the animals with anti-PD-L1 antibody (C and D). It is shown that there was an improvement in the combination therapy for both tumor size and survival in the combined treatment.

Shown in FIGS. 26 and 27, stimulatory PLGA NPs enhance the maturation of DC ($CD11b^+CD11c^+$) in tumors, characterized by up-regulation of MHC class II expression, and as shown in FIG. 27 by the uptake of fluorescently labeled stimulatory PLGA NPs in $CD11b^+CD11c^+$ dendritic cells.

The administration of nanoparticles also had the effect of decreasing frequencies of regulatory T cells (Treg $CD4^+$ $Foxp3^+$ cells) and increasing frequencies of Th17 ($CD4^+$ $IL17^+$) cells. A representative flow cytometry plot of tumor infiltrating $CD4^+$ T cells from B16F10 melanoma (upper) and MC38 (bottom) after ex vivo stimulation of cell stimulation cocktail for 5 h. is shown in FIG. 28. These data indicate a shift away from regulatory, suppressive T cells, to increased presence of pro-inflammatory T cell populations.

Discussion

We interrogated the phenotypic and functional characteristics of tumor-infiltrating $CD8^+$ T cells in melanoma and colon cancer tumor models, and the results demonstrated that stimulatory PLGA NPs elicited potent $CD8^+$ T cell response in both B16F10 melanoma and MC38 murine colon cancer models with markedly increased TNFα and IFNγ producing $CD8^+$ T cell population. The results further indicated that stimulatory PLGA NP is capable of driving T cell response strongly biased toward central memory (CD44$^{hi}$CD62L$^{hi}$) and effector memory (CD44$^{hi}$CD62L$^{low}$) populations in both tumors. Importantly, the nanoparticle elicits the potent self-specific CD8$^+$ T cell response by driving CD8$^+$ T cells differentiation into effector memory (CD44$^{hi}$CD62L$^{low}$) phenotype. The expression of surface activation markers (CD44, CD69 and CD25) has been observed in self-specific CD8$^+$ T cells. The function of self-specific CD8$^+$ T cells are restored by nanoparticles, as evident by the enhanced cytokine production of TNFα and IFNγ.

The stimulatory PLGA NPs are able to modulate the tumor microenvironment by up-regulating a variety of cytokines and chemokines, which are critical for the activation of dendritic cells (DCs) and recruitment of innate effectors and T cells into the tumor site. Notably, there is synergistic enhancement of cross-presentation by DC and proliferation of OT1-specific CD8$^+$ T cells after the treatment of stimulatory PLGA NPs containing TLR2 and NOD2 agonist.

The stimulatory PLGA NPs could increase the uptake efficiency of TLR2 and NOD2 agonists by DCs, thus providing stronger adjuvant effect, which is demonstrated by FACs analysis that the profound increase of fluorescence intensity in DCs after coincubation with NP encapsulated rhodamine-labeled TLR2 and NOD2 agonists compared to those co-incubated with soluble rhodamine-labeled TLR2 and NOD2 agonists The increased frequencies of Th17 (CD4$^+$IL17$^+$) cells and reduced frequencies in Treg (CD4$^+$Foxp3$^+$) cells have been observed after PLGA NP treatment, which presumably played a role in breaking the tolerance of self-specific CD8$^+$ T cells.

What is claimed is:

1. A method of treating melanoma or colon cancer, comprising the step of administering a therapeutically effective dose of a composition for the delivery of immunotherapeutic agents, comprising:
   a polymeric nanoparticle comprising:
     poly(lactic-co-glycolic)acid (PLGA);
     a payload comprising an effective dose of PAM3CSK4, L18-MDP, and IL-2; and
     an agonistic anti-CD28 antibody,
   wherein:
   the polymeric nanoparticle encapsulates the payload,
   the antibody is conjugated to the surface of the polymeric nanoparticle, and
   the effective dose of the composition comprises IL-2 at a concentration of up to 50 μg/kg body weight and PAM3CSK4 and L18-MDP in a 1:1 weight ratio.

2. The method of claim 1, wherein the therapeutically effective dose of the composition is administered in combination with an effective dose of an inhibitor of a T cell checkpoint protein.

3. A method of treating melanoma or colon cancer, comprising the step of administering a therapeutically effective dose of a composition for the delivery of immunotherapeutic agents, comprising:
   a polymeric nanoparticle comprising:
     poly(lactic-co-glycolic)acid (PLGA);
     a payload comprising an effective dose of PAM3CSK4, L18-MDP, and IL-2; and
     an agonistic anti-CD28 antibody,
   wherein:
   the polymeric nanoparticle encapsulates the payload,
   the antibody is conjugated to the surface of the polymeric nanoparticle, and
   the effective dose of the composition comprises IL-2 up to 50 μg/kg body weight, PAM3CSK4 up to 50 μg/kg body weight, and L18-MDP up to 50 μg/kg body weight.

4. The method of claim 3, wherein the therapeutically effective dose of the composition is administered in combination with an effective dose of an inhibitor of a T cell checkpoint protein.

5. A method of treating melanoma or colon cancer, comprising the step of administering a therapeutically effective dose of a composition for the delivery of immunotherapeutic agents, comprising:
   a polymeric nanoparticle comprising:
     poly(lactic-co-glycolic)acid (PLGA);
     a payload comprising an effective dose of IL-2, PAM3CSK4, and L18-MDP; and
     an agonistic anti-CD28 antibody,
   wherein:
   the polymeric nanoparticle encapsulates the payload, the antibody is conjugated to the surface of the polymeric nanoparticle, IL-2 is present at a concentration of up to 50 lag/kg body weight and the weight:weight:weight ratio of IL-2: PAM3CSK4:L18-MDP is 1:2:2; 1:1:1; 1:2:1; 1:1:2; 1:3:3; 1:2:3; 1:3:2; 1:1:3; or 1:3:1.

* * * * *